United States Patent
Douglas

(10) Patent No.: US 10,744,007 B2
(45) Date of Patent: *Aug. 18, 2020

(54) ALIGNMENT SYSTEM FOR MULTIPLE BRANCH ENDOGRAFTS

(71) Applicant: Red Vascular Technologies, LLC, Scottsdale, AZ (US)

(72) Inventor: Myles Douglas, Gardnerville, NV (US)

(73) Assignee: Red Vascular Technologies, LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/152,279

(22) Filed: Oct. 4, 2018

(65) Prior Publication Data

US 2019/0029849 A1 Jan. 31, 2019

Related U.S. Application Data

(63) Continuation of application No. 15/583,851, filed on May 1, 2017, now Pat. No. 10,111,765, which is a
(Continued)

(51) Int. Cl.
*A61F 2/856* (2013.01)
*A61F 2/07* (2013.01)
(Continued)

(52) U.S. Cl.
CPC .............. *A61F 2/856* (2013.01); *A61F 2/07* (2013.01); *A61F 2/954* (2013.01); *A61F 2/966* (2013.01);
(Continued)

(58) Field of Classification Search
CPC ............................. A61F 2/07; A61F 202/065
(Continued)

(56) References Cited

U.S. PATENT DOCUMENTS 5,954,764 A 9/1999 Parodi
6,579,309 B1 6/2003 Loos et al.
(Continued)

FOREIGN PATENT DOCUMENTS

| WO | WO-2006036690 A1 | 4/2006 |
| WO | WO-2006088675 A1 | 8/2006 |
| WO | WO-2009105699 A1 | 8/2009 |

OTHER PUBLICATIONS

Notice of Allowance dated Feb. 1, 2017 for U.S. Appl. No. 14/684,282.
Office Action dated Jun. 3, 2016 for U.S. Appl. No. 14/684,282.

*Primary Examiner* — Suzette J Gherbi
(74) *Attorney, Agent, or Firm* — Wilson Sonsini Goodrich & Rosati

(57) ABSTRACT

A nonmodular endograft system for treating aortic aneurysms involving bilateral renal arteries can include a main fabric cover that is sealed, coupled, or integral, with first and second branch fabric covers. The system can be configured so that after the main cover is expanded in the aorta, and after the two branch covers are respectively expanded in the renal arteries such that (i) the first cover ostium is substantially aligned with the first renal ostium, and (ii) the second cover ostium is not substantially aligned with the second renal ostium, then aortic blood flows from the main cover into each of the branch covers.

11 Claims, 19 Drawing Sheets

Related U.S. Application Data continuation of application No. 14/684,282, filed on Apr. 10, 2015, now Pat. No. 9,662,232.

(60) Provisional application No. 61/978,772, filed on Apr. 11, 2014.

(51) Int. Cl.
  *A61F 2/954* (2013.01)
  *A61F 2/966* (2013.01)
  *A61F 2/06* (2013.01)

(52) U.S. Cl.
  CPC ...... *H05K 999/99* (2013.01); *A61F 2002/061* (2013.01); *A61F 2002/065* (2013.01); *A61F 2002/067* (2013.01); *A61F 2210/0014* (2013.01); *A61F 2250/0098* (2013.01)

(58) Field of Classification Search
  USPC .............................................. 623/1.35–1.51
  See application file for complete search history.

(56) References Cited

U.S. PATENT DOCUMENTS

| | | | |
|---|---|---|---|
| 6,908,477 B2 | 6/2005 | McGuckin et al. | |
| 6,962,602 B2 | 11/2005 | Vardi et al. | |
| 7,691,135 B2 | 4/2010 | Shaolian et al. | |
| 7,699,883 B2 | 4/2010 | Douglas | |
| 7,771,462 B1 | 8/2010 | Davidson et al. | |
| 8,221,494 B2* | 7/2012 | Schreck | A61F 2/852 623/1.35 |
| 9,610,182 B2 | 4/2017 | Douglas | |
| 9,662,232 B2* | 5/2017 | Douglas | A61F 2/954 |
| 10,111,765 B2* | 10/2018 | Douglas | A61F 2/954 |
| 2003/0130720 A1* | 7/2003 | DePalma | A61F 2/07 623/1.13 |
| 2004/0030378 A1* | 2/2004 | Khosravi | A61F 2/07 623/1.13 |
| 2006/0247761 A1* | 11/2006 | Greenberg | A61F 2/07 623/1.16 |
| 2007/0244547 A1* | 10/2007 | Greenan | A61F 2/07 623/1.35 |
| 2007/0260217 A1 | 11/2007 | Von et al. | |
| 2008/0033525 A1 | 2/2008 | Shaked et al. | |
| 2008/0167704 A1* | 7/2008 | Wright | A61F 2/07 623/1.12 |
| 2008/0171934 A1* | 7/2008 | Greenan | A61B 5/6857 600/411 |
| 2008/0243233 A1 | 10/2008 | Ben-Muvhar et al. | |
| 2008/0255581 A1 | 10/2008 | Bourang et al. | |
| 2008/0269867 A1 | 10/2008 | Johnson | |
| 2009/0043377 A1* | 2/2009 | Greenberg | A61F 2/07 623/1.35 |
| 2009/0216315 A1 | 8/2009 | Schreck et al. | |
| 2010/0063576 A1* | 3/2010 | Schaeffer | A61F 2/07 623/1.13 |
| 2010/0121429 A1* | 5/2010 | Greenan | A61F 2/07 623/1.15 |
| 2010/0174139 A1 | 7/2010 | Windheuser et al. | |
| 2010/0241211 A1 | 9/2010 | Douglas | |
| 2010/0268327 A1* | 10/2010 | Bruszewski | A61F 2/07 623/1.18 |
| 2011/0015718 A1 | 1/2011 | Schreck | |
| 2011/0054586 A1 | 3/2011 | Mayberry et al. | |
| 2011/0270378 A1* | 11/2011 | Bruszewski | A61F 2/07 623/1.15 |
| 2011/0301693 A1* | 12/2011 | Hartley | A61F 2/07 623/1.35 |
| 2011/0313504 A1* | 12/2011 | Golding | A61F 2/07 623/1.11 |
| 2012/0271401 A1* | 10/2012 | Bruszewski | A61F 2/07 623/1.15 |
| 2012/0271410 A1 | 10/2012 | Douglas | |
| 2013/0079870 A1* | 3/2013 | Roeder | A61F 2/07 623/1.35 |
| 2014/0277348 A1* | 9/2014 | Roeder | A61F 2/07 623/1.11 |
| 2015/0173923 A1* | 6/2015 | Mayberry | A61F 2/07 623/1.11 |

* cited by examiner

ALIGNMENT SYSTEM FOR MULTIPLE BRANCH ENDOGRAFTS

CROSS-REFERENCE TO RELATED APPLICATIONS

This application is a continuation of U.S. patent application Ser. No. 15/583,851, filed May 1, 2017, now U.S. Pat. No. 10,111,765, which is a continuation of U.S. patent application Ser. No. 14/684,282, filed Apr. 10, 2015, now U.S. Pat. No. 9,662,232, which claims priority from U.S. Provisional Application No. 61/978,772, filed on Apr. 11, 2014, the entire content of which are hereby incorporated by reference.

FIELD OF THE INVENTION

The subject technology relates generally to implantable devices for interventional therapeutic treatment and, more particularly, to a branch endograft and delivery system for the treatment of disease involving branching vessels.

BACKGROUND OF THE INVENTION

Endoluminal repair or exclusion of aneurysms, such as in the aorta, has been performed in recent years. Endoluminal aortic aneurysm exclusion can correct a life-threatening disease in a minimally invasive manner in order to effectuate a patient's quick and complete recovery. Various vascular grafts exist that have been used to exclude aortic aneurysms.

The aorta is the largest artery in the body and is responsible for delivering blood from the heart to the organs of the body. The aorta includes the thoracic aorta, which arises from the left ventricle of the heart, passes upward, bends over and passes down towards the thorax, and the abdominal aorta which passes through the thorax and through the abdomen to about the level of the fourth lumbar vertebra, where it divides into the two common iliac arteries. The thoracic aorta is divided into the (i) ascending aorta, which arises from the left ventricle of the heart, (ii) the aorta arch, which arches from the ascending aorta and (iii) the descending aorta which descends from the aorta arch towards the abdominal aortic.

A thoracic aortic aneurysm ("TAA") is a widening, bulge, or ballooning out of a portion of the thoracic aorta, usually at a weak spot in the aortic wall. If left untreated, the aneurysm may progressively expand until the vessel dissects or ruptures. This may lead to severe and even fatal hemorrhaging. Factors leading to thoracic aorta aneurysms include hardening of the arteries (atherosclerosis), hypertension, congenital disorders such as Marfan's syndrome, trauma, or less commonly syphilis. Thoracic aorta aneurysms occur in the ascending aorta about 25% of the time, the aortic arch about 25% of the time and in the descending aorta about 50% of the time.

Treatment of thoracic aorta aneurysms depends upon the location of the aneurysm. For aneurysms in the ascending aorta or aortic arch, surgery is typically required to replace the aorta with an artificial vessel. This surgical procedure typically requires exposure of the aorta and the use of a heart-lung machine. If the aortic arch is involved, a specialized technique called "circulatory arrest" (i.e., a period without blood circulation while on life support) may be necessary. For aneurysms in the descending aorta, the vessel may also be replaced with an artificial vessel through surgery. In some circumstances, an endoluminal vascular graft may be used eliminating the need for open surgery.

Straight tube grafts have been used in the infrarenal abdominal aorta to exclude an aneurysmal sac from the blood stream, thereby resulting in the weakened aortic wall being protected by graft material. These straight tube grafts were initially unsupported; they employed stents at their proximal and distal ends to anchor the proximal and distal ends of the graft to the healthy portions of the aorta thereby leaving a midsection of the graft or prosthesis that did not have any internal support. Although this type of graft at first appeared to correct the aortic aneurysm, it met with many failures. The unsupported nature of its midsection allowed the graft to migrate distally as well as exhibit significant proximal leakage due to the enlargement of the aorta without adaptation of the graft, such as enlargement of the graft, to accommodate the change in diameter of the aorta.

Technical improvements in stent design led to "self-expanding" stents. In addition, later improvements produced Nitinol stents which have a "memory" capable of expanding to a predetermined size. Graft designers began to develop bifurcated grafts having limbs which extended into the iliac arteries. The development of bifurcated grafts allowed for the treatment of more complex aneurysms.

Many bifurcated grafts are of a two-piece or modular design. The two-piece designs often require the insertion of a contralateral limb through or a separate access site. These types of grafts are complex to deploy and have the potential for leakage at the connection site of the two limbs of the graft.

Endoluminal implantation is a common technique for implanting vascular grafts. Typically, this procedure involves percutaneously inserting a vascular graft or prosthesis by using a delivery catheter. This process eliminates the need for major surgical intervention, thereby decreasing the risks associated with vascular and arterial surgery.

BRIEF SUMMARY OF THE INVENTION

The subject technology is illustrated, for example, according to various aspects described below. Various examples of aspects of the subject technology are described as numbered clauses (1, 2, 3, etc.) for convenience. These are provided as examples, and do not limit the subject technology. It is noted that any of the dependent clauses may be combined in any combination, and placed into a respective independent clause. The other clauses can be presented in a similar manner.

1. A system for treating disease involving branching vessels of a mammal, comprising:
    a main graft assembly (i) having a lumen permitting fluid flow therethrough, and (ii) configured to expand within, and contact a wall of, a main vessel of a mammal; and
    a branch graft assembly comprising:
       a branch cover (i) having a lumen (cover lumen) permitting fluid flow therethrough; and (ii) configured to expand within, and contact a wall of, a branch vessel that branches from the main vessel;
       an expandable stent (branch stent) extending within the cover lumen; and
       a branch sheath (i) extending between the branch stent and the cover lumen, and (ii) constraining radial expansion of the branch stent within the cover lumen.
2. The system of clause 1, wherein the branch sheath at least partially surrounds the branch stent.
3. The system of clause 1, wherein a distal portion of the branch stent is coupled to a distal portion of the branch cover.

4. The system of clause 3, wherein the branch stent is coupled to the branch cover along at least part of a perimeter of the branch cover.

5. The system of clause 1, wherein distal movement of the branch sheath within the branch cover is inhibited by a coupling of the branch stent to the branch cover.

6. The system of clause 5, wherein the coupling is of a distal portion of the branch stent to a distal portion of the cover.

7. The system of clause 1, wherein the branch stent is self-expanding.

8. The system of clause 1, further comprising a delivery catheter (a) configured to be placed into the main vessel and (b) through which the main graft assembly is configured to extend.

9. The system of clause 8, further comprising an outer sheath through which the delivery catheter extends.

10. The system of clause 8, wherein the branch sheath extends through both an aperture in the catheter and an aperture in the main graft assembly.

11. The system of clause 8, wherein the branch sheath extends through an aperture in the catheter.

12. The system of clause 11, wherein the branch graft assembly is movable within the aperture.

13. The system of clause 11, wherein the aperture comprises a longitudinal groove in the catheter.

14. The system of clause 1, wherein the main graft assembly is coupled to the branch graft assembly.

15. The system of clause 1, wherein the branch sheath extends outside the main graft assembly.

16. The system of clause 1, wherein the branch sheath extends within the main graft assembly and into the branch cover through an aperture in the main graft assembly.

17. The system of clause 1, wherein the branch graft assembly is coupled to the main graft assembly.

18. The system of clause 1, wherein the branch stent is configured to expand radially against the branch cover upon release of the branch stent from the branch sheath by proximal movement of the branch sheath.

19. The system of clause 1, wherein the main graft assembly and the branch graft assembly are configured to lie substantially parallel to each other during delivery of the main graft assembly to the main vessel, and wherein the branch graft assembly is configured such that, while a proximal portion of the assembly remains within and/or in contact with the main graft assembly, the distal portion of the assembly moves away from the main graft assembly when the assembly is unconstrained by a sheath during delivery of the branch cover to the branch vessel.

20. The system of clause 1, further comprising an elongate member (branch delivery member) configured to extend through the branch cover and into the branch vessel.

21. The system of clause 20, further comprising an anchoring member, at a distal portion of the branch delivery member, that expands in and engages the branch vessel to resist axial movement of the anchoring member within the branch vessel.

22. The system of clause 1, wherein each of the main vessel and the branch vessel comprises an artery or a vein.

23. The system of clause 1, wherein the main graft assembly comprises (a) a main stent that is expandable and (b) a main cover that at least partially surrounds the main stent.

24. The system of clause 23, wherein each of the main cover and the branch cover comprises an impermeable or semipermeable fabric.

25. The system of clause 23, wherein the a main cover is coextensive with the branch cover.

26. The system of clause 23, wherein the main cover is coupled to the branch cover.

27. The system of clause 1, further comprising an elongate member (main delivery member) configured to extend through the main graft assembly into the main vessel.

28. The system of clause 1, further comprising a pusher that extends within the branch sheath and is configured to resist proximal movement of the branch stent within the branch sheath when a distal end of the pusher contacts a proximal end of the branch stent.

29. The system of clause 21, wherein the anchoring member self-expands upon release of the anchoring member from a lumen of a constraining member.

30. The system of clause 29, wherein the release of the anchoring member occurs by proximal movement of the constraining member relative to the anchoring member.

31. A method, of treating disease involving branching blood vessels of a mammal, comprising:
advancing distally into a first blood vessel of a mammal a main stent graft having a lumen permitting fluid flow therethrough;
expanding the main stent graft within, and contacting a wall of, the main vessel;
advancing through the main vessel, and into a branch vessel that branches from the main vessel, a branch graft assembly comprising:
a branch cover (i) having a lumen (cover lumen) permitting fluid flow therethrough;
an expandable stent (branch stent) extending within the cover lumen; and
a branch sheath (i) extending between branch stent and the cover lumen, and (ii) constraining radial expansion of the branch stent within the cover lumen; [0054] releasing the branch stent from within the branch sheath, thereby permitting expansion of the branch stent and branch cover such that the branch cover contacts a wall of the branch vessel.

32. The method of clause 31, wherein the branch sheath at least partially surrounds the branch stent.

33. The method of clause 31, wherein the releasing comprises moving the branch sheath proximally.

34. The method of clause 33, further comprising withdrawing the branch sheath from the mammal.

35. The method of clause 33, wherein the advancing of the main stent graft, the advancing of the branch graft assembly, and withdrawing of the branch sheath from the mammal after the releasing all occur through a single opening in skin of the mammal.

36. The method of clause 31, wherein the main stent graft and the branch graft assembly are advanced together into the main vessel within a delivery catheter.

37. A system for treating disease involving branching vessels of a mammal, comprising:
a main cover (i) having a main lumen permitting fluid flow therethrough, and (ii) configured to expand in, and contact a wall of, a main vessel of a mammal; and
a branch cover (i) having a branch lumen in fluid communication with the main lumen, and (ii) configured to expand in, and contact a wall of, a branch vessel that branches from the main vessel;
wherein the branch cover is coupled to the main cover at an opening in the main cover, and the branch cover has a longitudinal length extending from the opening to a distal end of the branch cover;

wherein the opening has a larger area than does a cross section of the branch lumen that is less than 80% of the length away from the opening.

38. The system of clause 37, wherein (i) the branch vessel is first branch vessel, (ii) the branch cover is a first branch cover; and (iii) the branch lumen is first branch lumen; and further comprising a second branch cover (i) having a second branch lumen, in fluid communication with the main lumen, and (ii) configured to expand in, and contact a wall of, a second branch vessel that branches from the main vessel.

39. The system of clause 37, wherein the opening has a larger area than does a cross section of the branch lumen that is less than 70% of the length away from the opening.

40. The system of clause 37, wherein the opening has a larger area than does a cross section of the branch lumen that is less than 60% of the length away from the opening.

41. The system of clause 37, wherein the opening has a larger area than does a cross section of the branch lumen that is less than 50% of the length away from the opening.

42. The system of clause 37, wherein the opening has a larger area than does a cross section of the branch lumen that is less than 40% of the length away from the opening.

43. The system of clause 37, wherein the opening has a larger area than does a cross section of the branch lumen that is less than 30% of the length away from the opening.

44. The system of clause 37, wherein the opening has a larger area than does a cross section of the branch lumen that is less than 25% of the length away from the opening.

45. The system of clause 37, wherein the opening has a larger area than does a cross section of the branch lumen that is less than 20% of the length away from the opening.

46. The system of clause 37, wherein the opening has a larger area than does a cross section of the branch lumen that is less than 15% of the length away from the opening.

47. The system of clause 37, wherein the opening has a larger area than does a cross section of the branch lumen that is less than 10% of the length away from the opening.

48. The system of clause 37, wherein the opening has a larger area than does a cross section of the branch lumen that is less than 5% of the length away from the opening.

49. The system of any of clauses 37-47, wherein the opening area is at least 10% larger than the area of the cross section of the branch lumen.

50. The system of any of clauses 37-47, wherein the opening area is at least 20% larger than the area of the cross section of the branch lumen.

51. The system of any of clauses 37-47, wherein the opening area is at least 30% larger than the area of the cross section of the branch lumen.

52. The system of any of clauses 37-47, wherein the opening area is at least 40% larger than the area of the cross section of the branch lumen.

53. The system of any of clauses 37-47, wherein the opening area is at least 50% larger than the area of the cross section of the branch lumen.

54. The system of any of clauses 37-47, wherein the opening area is at least 60% larger than the area of the cross section of the branch lumen.

55. The system of any of clauses 37-47, wherein the opening area is at least 70% larger than the area of the cross section of the branch lumen.

56. The system of any of clauses 37-47, wherein the opening area is at least 80% larger than the area of the cross section of the branch lumen.

57. The system of any of clauses 37-47, wherein the opening area is at least 90% larger than the area of the cross section of the branch lumen.

58. The system of any of clauses 37-47, wherein the opening area is at least 100% larger than the area of the cross section of the branch lumen.

59. The system of any of clauses 37-47, wherein the opening area is at least 120% larger than the area of the cross section of the branch lumen.

60. The system of any of clauses 37-47, wherein the opening area is at least 150% larger than the area of the cross section of the branch lumen.

61. The system of any of clauses 37-47, wherein the opening area is at least 180% larger than the area of the cross section of the branch lumen.

62. The system of any of clauses 37-47, wherein the opening area is at least 200% larger than the area of the cross section of the branch lumen.

63. The system of any of clauses 37-61, wherein fluid flow through the main lumen is substantially along a longitudinal axis of the main lumen, and the opening has a dimension along the longitudinal axis that is greater than a dimension of the opening along an axis transverse to the longitudinal axis.

64. The system of clause 62, wherein the transverse axis is perpendicular to the longitudinal axis.

65. The system of clause 37, further comprising:
an expandable stent extending within the main lumen; and
an expandable stent extending within the branch lumen.

66. The system of clause 37, wherein the branch cover is sealed to the main cover by at least one of sewing, thermal bonding, or gluing.

67. The system of clause 37, wherein the branch cover is integrally formed with the main cover.

68. The system of clause 37, wherein the branch cover and the main cover comprise a fabric.

69. The system of clause 37, wherein a junction between the branch cover and the main cover comprises a seal preventing blood cells from passing therethrough.

70. A system for treating disease involving branching vessels of a mammal, comprising:
a main cover (i) having a main lumen permitting fluid flow therethrough, and (ii) configured to expand in, and contact a wall of, a main vessel of a mammal; and
first and second branch covers, each (i) branching from the main cover at a respective cover ostium, (ii) having a respective branch lumen in fluid communication with the main lumen, and (ii) being configured to expand in, and contact a wall of, a respective branch vessel that branches from the main vessel at a respective vessel ostium;
wherein the main and branch covers are configured such that, after the main cover is expanded in the main vessel, and after the two branch covers are expanded in the respective branch vessels such that (i) the first cover ostium is substantially aligned with the first vessel ostium, and (ii) the second cover ostium is not substantially aligned with the second vessel ostium, then blood flows from the main cover into each of the branch covers.

71. The system of clause 73, wherein the main cover and the two branch covers each comprises fabric, and, prior to insertion of the main cover into the main vessel, the fabric of each of the two branch covers is continuous with, integrally formed with, or permanently attached to, the fabric of the main cover.

72. The system of clause 73, wherein (i) the main cover and the two branch covers each comprises a fabric, (ii) the second branch cover has a longitudinal length extending from the second cover ostium to a distal end of the second branch cover, and (iii) a cross sectional area of the second branch lumen at the second cover ostium is larger than is a cross sectional area of the second branch lumen that is less than 80% of the length away from the opening.

73. The system of clause 73, wherein (i) the second branch cover comprises a fabric, and (ii) a cross sectional dimension of the second branch cover decreases from the second cover ostium toward a distal end of the second branch cover.

74. The system of clause 73, wherein (i) the second branch cover tapers from the second cover ostium toward a distal end of the second branch cover.

75. The system of any of the above clauses, wherein the main vessel comprises an aorta, and each of any of the branch vessels comprises a renal artery.

76. A method for treating disease involving branching vessels of a mammal, comprising:

inserting into a main vessel a main cover (i) having a main lumen permitting fluid flow therethrough and (ii) configured to expand in, and contact a wall of, the main vessel;

inserting into a first branch vessel, that branches from the main vessel at a first vessel ostium, a first branch cover that (i) branches from the main cover at a first cover ostium, (ii) has a first branch lumen in fluid communication with the main lumen, and (ii) is configured to expand in, and contact a wall of, the first branch vessel;

inserting into a second branch vessel, that branches from the main vessel at a second vessel ostium, a second branch cover that (i) branches from the main cover at a second cover ostium, (ii) has a second branch lumen in fluid communication with the main lumen, and (ii) is configured to expand in, and contact a wall of, the second branch vessel;

wherein, after the inserting of the first and second branch covers, (i) the first cover ostium is substantially aligned with the first vessel ostium, (ii) the second cover ostium is not substantially aligned with the second vessel ostium, and (iii) blood flows from the main cover into each of the first and second branch covers.

77. The method of clause 69, wherein the main cover and the two branch covers each comprises fabric, and, prior to insertion of the main cover into the main vessel, the fabric of each of the two branch covers is continuous with, integrally formed with, or permanently attached to, the fabric of the main cover.

78. A method for treating disease involving branching vessels of a mammal, comprising:

inserting into a main vessel a main cover (i) having a main lumen permitting fluid flow therethrough and (ii) configured to expand in, and contact a wall of, the main vessel;

inserting into each of first and second branch vessels, each branching from the main vessel at a respective vessel ostium, a respective branch cover that (i) branches from the main cover at a respective cover ostium, (ii) has a respective branch lumen in fluid communication with the main lumen, and (ii) is configured to expand in, and contact a wall of, the respective branch vessel;

wherein, after the inserting of the two branch covers, (i) the first cover ostium is substantially aligned with the first vessel ostium, (ii) the second cover ostium is not substantially aligned with the second vessel ostium, and (iii) blood flows from the main cover into each of the first and second branch covers.

79. The method of clause 71, wherein the main cover and the two branch covers each comprises fabric, and, prior to insertion of the main cover into the main vessel, the fabric of each of the two branch covers is continuous with, integrally formed with, or permanently attached to, the fabric of the main cover.

80. The method of any of the above method clauses, wherein the main vessel comprises an aorta, and each of any of the branch vessels comprises a renal artery.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION OF THE INVENTION

Figure 1:
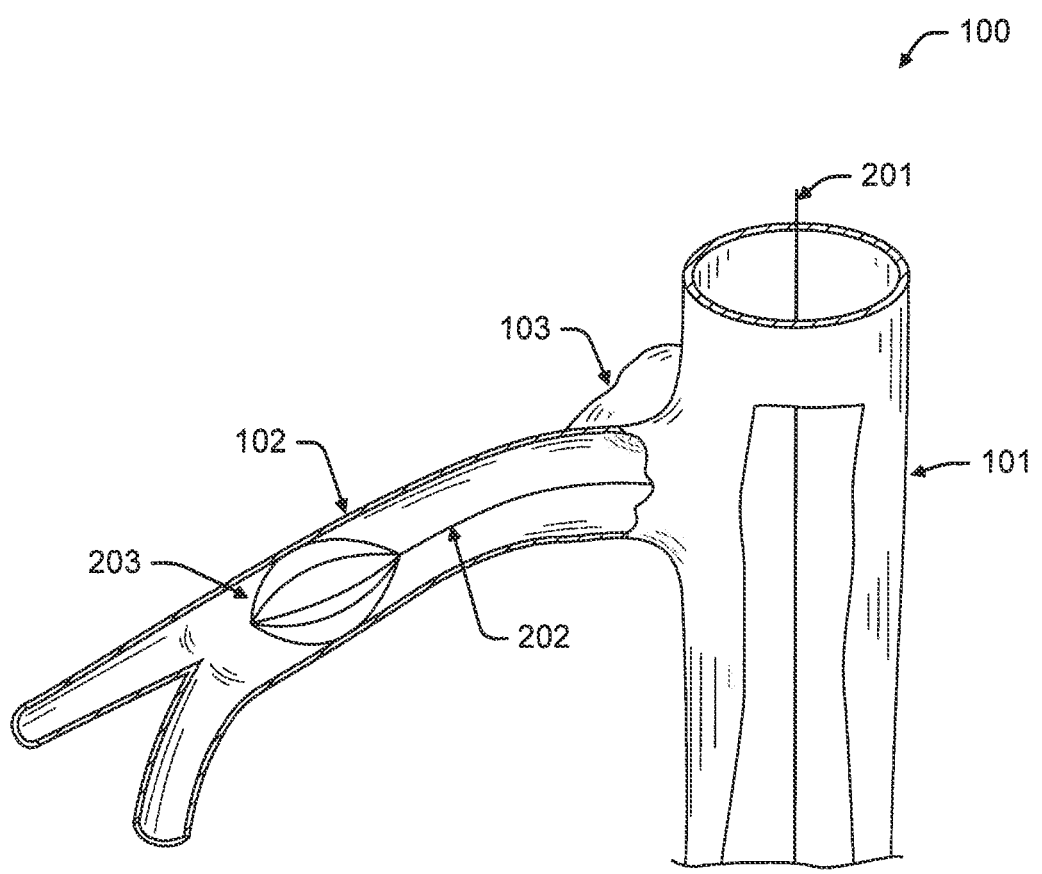
FIG. 1 depicts a main vessel with a main delivery member therein and a branching vessel with a branch delivery member therein.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology. Like components are labeled with identical element numbers for ease of understanding.

Aortic aneurysms are a weakening in the wall of the aorta which causes this large blood vessel to expand. At various diameters, this potentially can cause this vessel to rupture causing significant blood loss and death. The aorta is responsible for transporting blood from the heart to the various organs in the body. Various organs (i.e., liver, lungs, kidneys, brain) are supplied blood by branches from the aorta which are of various sizes and length. At times, aneurysms may be so extensive as to include or involve a branch or branches of blood vessels which supply blood to various organs.

Historically, the treatment of aortic aneurysms involved the surgical excision of the aneurysm. If one or more of the important organ branches was involved, a "side branch," made of various materials, was typically attached to the larger main bypass graft by sewing the smaller caliber "side branch" graft to the main bypass graft.

Grafts used in endograft repair of aortic aneurysms, a minimally invasive technique, are typically inserted into a femoral artery (although they could be inserted into another artery, such as the subclavian) and moved to the area of the aneurysm using various methods of deployment. Once in position, the graft is deployed at the aneurysm site, thereby eliminating blood flow into the aneurysm and eliminating the danger of rupture. If the aneurysm, however, involves one of the major organ branches, using the endovascular technique described above becomes more difficult.

Conventional methods for treating aortic aneurysms that involve major organ branches include the use of modular aortic endografts. Modular aortic endografts are constructed with what are called "fenestrations" or small "holes" or "windows" in the main body of the endograft which coincide with the take off or origin of the involved branch of the aorta. Through these "fenestrations," smaller endografts are deployed so as to continue blood flow to the major organ and assure exclusion of the aneurysm. The smaller endografts that are deployed through the "fenestrations" are prone to leak at the attachment point, dislodge, and/or migrate downstream. Any one of these situations can create a large "endoleak" which may repressurize the aneurysm sac and cause rupture.

In addition, by excluding aneurysms from blood flow with a modular graft in an attempt to "cure" the condition, the morphology of the aorta can change. Post-grafting aortic changes may include shrinkage, changes in shape, curvature, and/or size. The changes may generate significant stresses on the graft and cause dislodgement of not only the entire endograft, but also of any modular limb or side branch. Such dislodgment may cause the complete failure of the endograft, thereby resulting in a possible rupture of the aneurysm.

Although one-piece bifurcated grafts largely eliminate leakage and graft failure at the suture or juncture site associated with two piece bifurcated grafts that join together two separate grafts to form the bifurcated graft, past delivery methods for one-piece bifurcated grafts have been suboptimal, often requiring access to both limbs for unsheathing bifurcated grafts.

The implantable device of the subject technology solves some or all of the foregoing problems by using a one piece, "non-modular" branched endograft that is not prone to separation or leakage. The non-modular branched endograft provides almost immediate blood flow to the interested organ and significantly improves the integrity of the entire endograft by essentially eliminating all likelihood that the endograft may leak, migrate, or be disrupted. The longevity of the non-modular branched endograft is thus improved, ensuring the success of the procedure. In addition, although the branched endograft of the subject technology may be constructed as a one-piece endograft, it is understood that the branched endograft may be constructed from modular components that are coupled to each other.

FIG. 1 illustrates a schematic representation of a first blood vessel 101 and a second blood vessel 102, the second blood vessel 102 branching from the first blood vessel 101. The main vessel 101 and branch vessel 102 may comprise an artery or a vein. For example, the main vessel 101 may be a thoracic or abdominal aorta and the branch vessel 102 may be a visceral artery. An aneurysm 103 is illustrated adjacent the main vessel 101 and the branch vessel 102. As will be explained, in more detail below, the branched endograft 300, as shown in FIG. 10, may be used to span the aneurysm 103.

Figure 10:
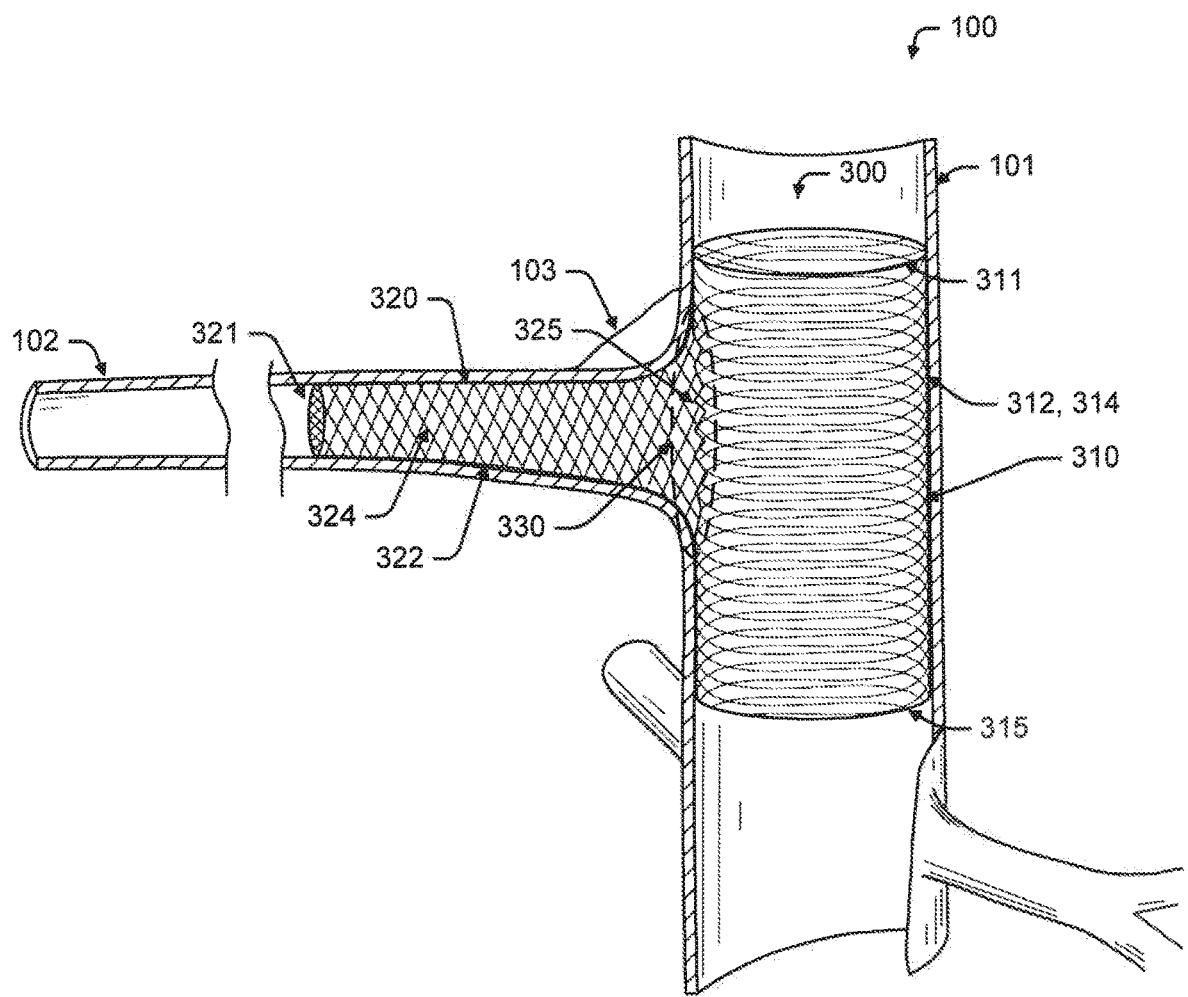
FIG. 10 depicts a deployed endograft, according to one aspect of the subject technology.

Referring to FIG. 10, the branched endograft 300 may be used for treating disease involving branching vessels 100 of a mammal. The branched endograft 300 may include a main graft assembly 310 and one or more branch graft assemblies 320.

The main graft assembly 310 may include a main cover 312 and a main stent 314. The main stent 314 may be expandable and the main cover 312 may at least partially surround the main stent 314.

The main stent 314 may comprise a tubular wire support structure that may be configured to be expanded via an internal expanding device (e.g., a balloon) or may be wholly or partially self expandable. For example, a self expandable tubular support may be formed from a shape memory alloy that can be deformed from an original, heat-stable configuration to a second heat-unstable configuration. The main stent 314 may be formed from a piece of metal tubing that is laser cut. The main stent 314 may comprise one or more wires and other self-expandable configurations known to those of skill in the art. Self expandable tubular structures may conveniently be formed with a series of axially adjacent segments. Each segment generally comprises a zig-zag wire frame having a plurality of apexes at its axial ends, and wire struts extending therebetween. The opposing apexes of adjacent segments may be connected in some or all opposing apex pairs, depending upon the desired performance. In another example, one or more of the individual segments may be separated from adjacent segments and retained in a spaced apart, coaxial orientation by the main cover 312 or other graft material. The main stent 314 need not extend through the entire axial length of the main cover 312.

Further referring to FIG. 10, the main cover 312 may have a generally tubular body having a distal end 311 which defines a distal opening, and a proximal end 315 which defines a proximal opening. As used herein, the terms proximal and distal are defined relative to a deployment catheter, such that the distal end 311 is positioned further away from the deployment catheter than the proximal end 315. The main cover 312 may be manufactured from an impermeable or semipermeable fabric and may be formed from any of a variety of synthetic polymeric materials, or combinations thereof, including ePTFE, PE, PET, Urethane, Dacron, nylon, polyester or woven textiles.

The main cover 312 may have a lumen to permit fluid flow therethrough and may be configured to expand within, and contact a wall of, the main vessel 101. In one aspect, the material of the main cover 312 may be sufficiently porous to permit ingrowth of endothelial cells, thereby providing more secure anchorage of the main cover 312 and potentially reducing flow resistance, sheer forces, and leakage of blood around the main cover 312. The porosity characteristics of the main cover 312 may be either homogeneous throughout the axial length of the main cover 312, or may vary according to the axial position of the main cover 312. For example, it may be advantageous to configure the distal end 311 and the proximal end 315 of the main cover 312, which seat against the main vessel wall 101, to encourage endothelial growth, or, to permit endothelial growth to infiltrate portions of the main cover 312 in order to enhance anchoring and minimize leakage. Because anchoring may be less of an issue, the central portion of the main cover 312, which may span the aneurysm, may be configured to maximize lumen diameter and minimizing blood flow through the main cover 312 wall and therefore, may either be generally nonporous, or provided with pores of relatively lower porosity.

Figure 11:
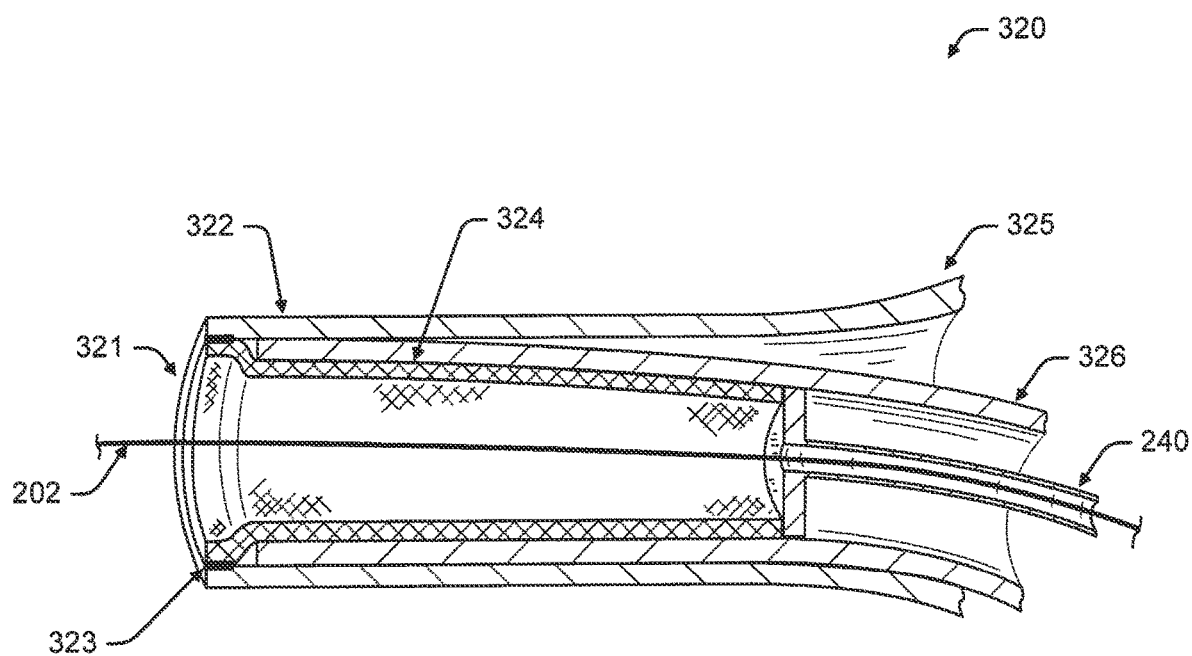
FIG. 11 depicts a cross section of a branch graft assembly, according to one aspect of the subject technology.

Referring to FIG. 11, the branch graft assembly 320 may include a branch cover 322, a branch stent 324, and a branch sheath 326.

The branch cover or cover lumen 322 may comprise a generally tubular body having a proximal end 325 which defines a proximal opening, and a distal end 321 which defines a distal opening. The branch cover 322 may be manufactured from an impermeable or semipermeable fabric and may be formed from any of a variety of synthetic polymeric materials, or combinations thereof, including ePTFE, PE, PET, Urethane, Dacron, nylon, polyester or woven textiles.

The branch cover 322 may have a lumen to permit fluid flow therethrough and may be configured to expand within, and contact a wall of, the branch vessel 102. In one aspect, the material of the branch cover 322 may be sufficiently porous to permit ingrowth of endothelial cells, thereby providing more secure anchorage of the branch cover 322 and potentially reducing flow resistance, sheer forces, and leakage of blood around the branch cover 322. The porosity characteristics of the branch cover 322 may be either homogeneous throughout the axial length of the branch cover 322, or may vary according to the axial position of the branch cover 322. For example, it may be advantageous to configure a distal end 321 of the branch cover 322, which seats against the branch vessel wall 102, to encourage endothelial growth, or, to permit endothelial growth to infiltrate portions of the branch cover 322 in order to enhance anchoring and minimize leakage. Because anchoring may be less of an issue, the central or proximal portion of the branch cover 322, which may span the aneurysm, may be configured to maximize lumen diameter and minimizing blood flow through the branch cover 322 wall and therefore, may either be generally nonporous, or provided with pores of relatively lower porosity.

Referring again to FIG. 10, the branch graft assembly 320 may be coupled to the main graft assembly 310. Specifically, the branch cover 322 may be coupled to the main cover 312. For example, the proximal end 325 of the branch cover 322 may be coupled to the main cover 312 at a region 330 that is intermediate of the proximal end 315 and the distal end 311 of the main cover 312. The coupling region 330 may be configured to allow fluid communication between the lumen of the main cover 312 and the lumen of the branch cover 322 via an aperture, thereby making the main cover 312 and the branch cover 322 integral or coextensive, i.e., one piece and non-modular. The coupling region 330 may also be configured to allow the branch cover 322 to articulate and permit sufficient flexibility between the main cover 312 and the branch cover 322 such that the branch cover 322 may be placed within the branch vessel 102 while the main cover 312 is positioned within the main vessel 101

Referring to FIG. 11, the branch stent 324 may comprise an expandable stent that extends within the branch cover 312. The branch stent 324 may be configured to expand radially against the branch cover 312 upon release of the branch stent 324 from the branch sheath 326, as discussed further below, by proximal movement of the branch sheath 326. After deployment, the branch stent 324 may support the branch cover 322 in the branch vessel 102 such that the branch cover 322 makes sufficient contact against the branch vessel wall 102.

The branch stent 324 may comprise a tubular wire support structure that may be configured to be expanded via an internal expanding device (e.g., a balloon) or may be wholly or partially self expandable. For example, a self expandable tubular support may be formed from a shape memory alloy that can be deformed from an original, heat-stable configuration to a second heat-unstable configuration. The branch stent 324 may be formed from a piece of metal tubing that is laser cut. The branch stent 324 may comprise one or more wires and other self-expandable configurations known to those of skill in the art. Self expandable tubular structures may conveniently be formed with a series of axially adjacent segments. Each segment generally comprises a zig-zag wire frame having a plurality of apexes at its axial ends, and wire struts extending therebetween. The opposing apexes of adjacent segments may be connected in some or all opposing apex pairs, depending upon the desired performance. In another example, one or more of the individual segments may be separated from adjacent segments and retained in a spaced apart, coaxial orientation by the branch cover 322 or other graft material. The branch stent 324 need not extend through the entire axial length of the branch cover 322.

A distal portion of the branch stent 324 may be coupled or attached to a distal portion of the branch cover 322 along at least part of a perimeter of the branch cover 322. Coupling 323 of the branch stent 324 to the branch cover 322 may be achieved by clipping, sewing, bonding, gluing, heat fusing, or other coupling methods as may be known by a person of ordinary skill The branch sheath 326 may comprise a flexible tubular sheath extending between the branch stent 324 and the branch cover 322. The branch sheath 326 may be configured to compress or constrain the radial expansion of the branch stent 324 within the branch cover 322 by at least partially surrounding the branch stent 324. The branch sheath 326 may be configured to extend within and through the main graft assembly 310, toward and into the branch graft assembly 320, via the aperture of the coupling region 330, as shown in FIGS. 6-9.

Suitable dimensions for the main cover 312 and branch cover 322 can be readily selected taking into account the natural anatomical dimensions of the treatment area, i.e., the main vessel 101 and the branch vessel 102. For example, for treatment of an aortic aneurysm, account of the natural anatomical dimensions in the thoracic aorta and its principal branches (i.e., the innomate artery, left carotid and subclavian arteries) would be taken. In this example, the main cover 312 will have a fully expanded diameter within the range of from about 20 mm to about 50 mm, and a length within the range of from about 5 cm to about 20 cm for use in the descending aorta. Lengths outside of these ranges may be used, for example, depending upon the length of the aneurysm to be treated, the tortuosity of the aorta in the affected region and the precise location of the aneurysm. Shorter lengths may be desirable for the main cover 312 when treating aneurysms in the ascending aorta or the aortic arch as will be appreciated by those of skill in the art.

The branch cover 322 for use in the subclavian artery will generally have a length within the range of from about 10 mm to about 20 mm, and a fully expanded diameter within the range of from about 2 cm to about 10 cm. Both the main cover 312 and the branch cover 322 will preferably have a fully expanded diameter in an unconstrained state which is larger than the inside diameter of the vessel within which they are to be deployed, in order to maintain positive pressure on the vessel wall.

The minimum length for the main cover 312 will be a function of the size of the aneurysm. Preferably, the axial length of the main cover 312 will exceed the length of the aneurysm, such that a seating zone is formed at each end of the main cover 312 within which the main cover 312 overlaps with healthy vascular tissue beyond the proximal and distal ends of the aneurysm.

Figure 3:
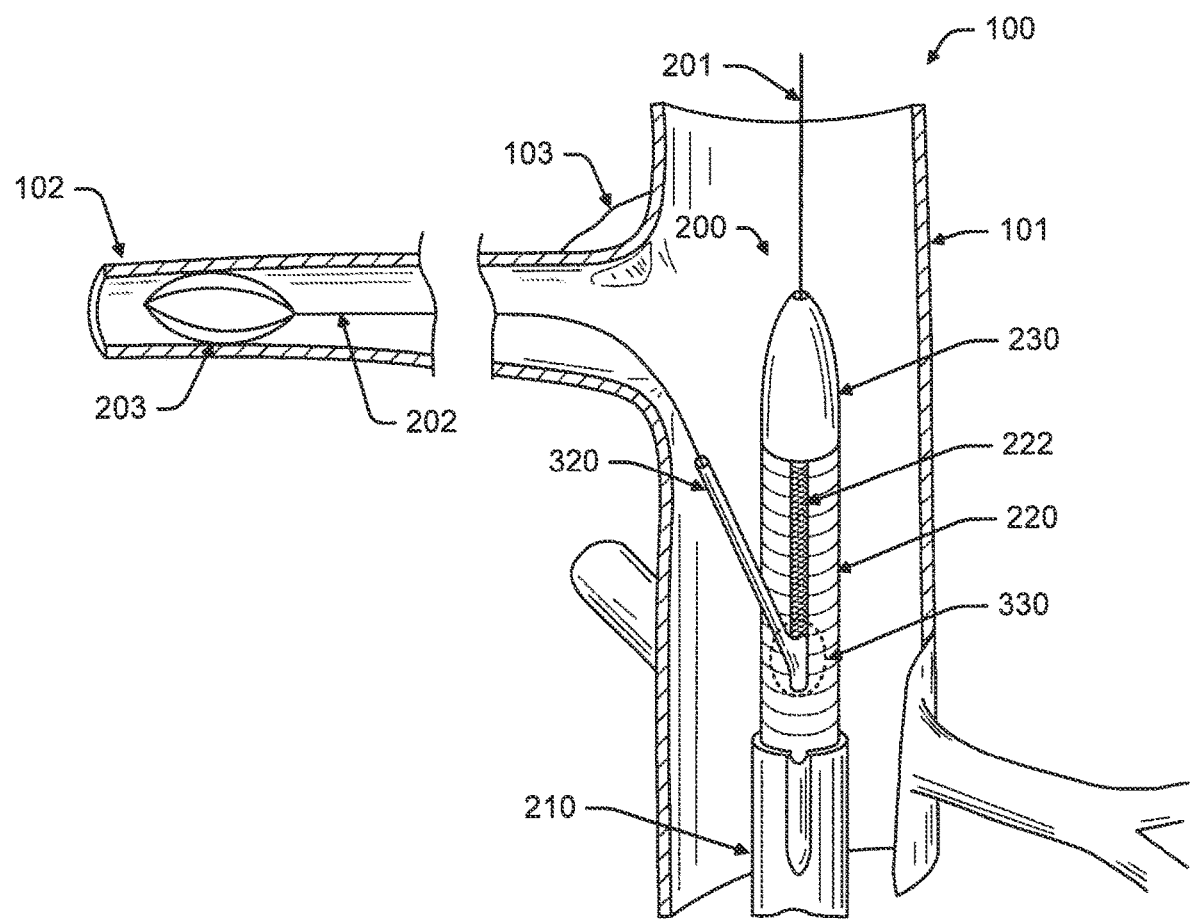
FIG. 3 depicts an endograft delivery system with an outer sheath withdrawn proximally, according to one aspect of the subject technology.
Figure 4:
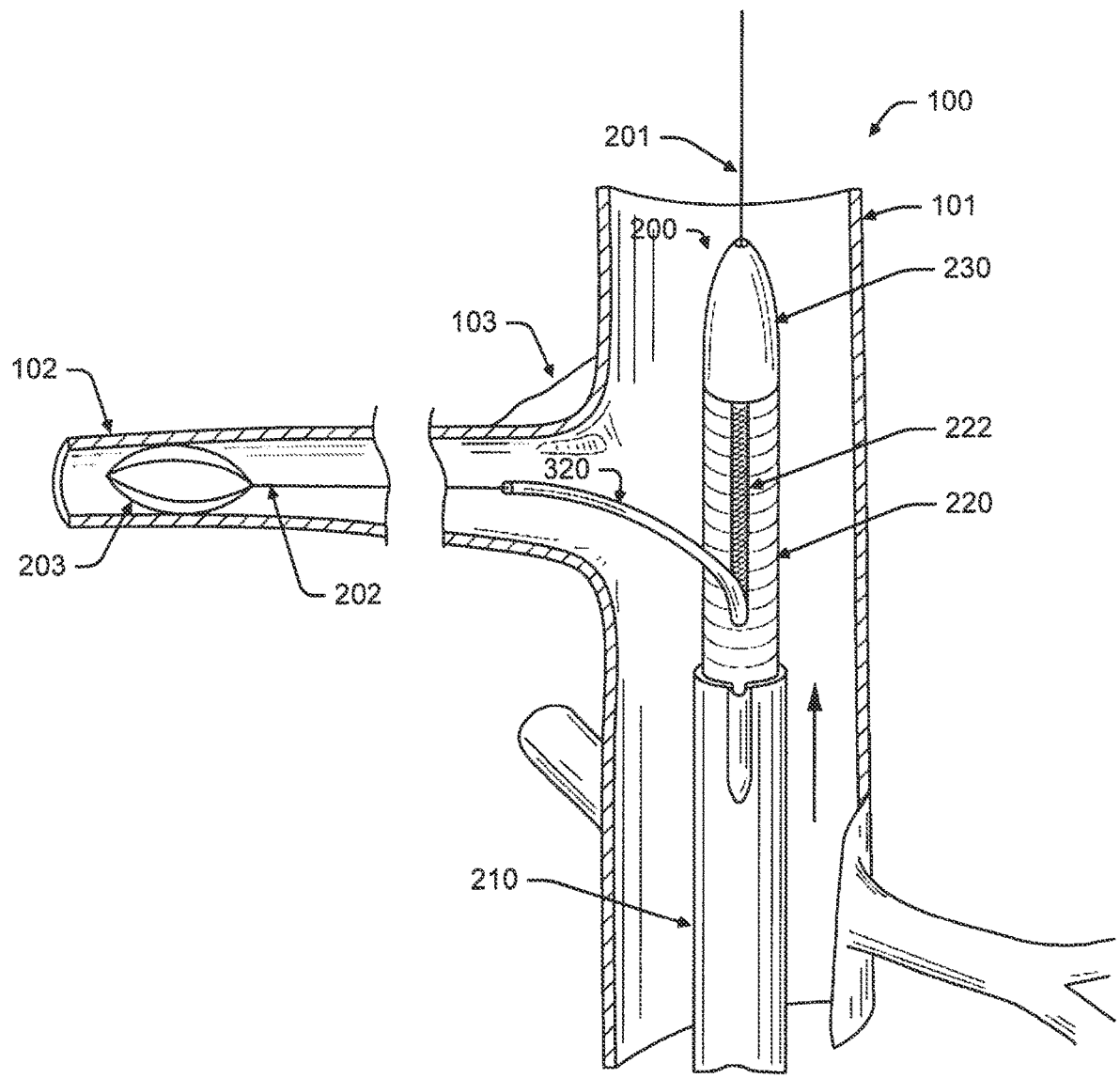
FIG. 4 depicts an endograft delivery system positioned in the vicinity of a branch vessel, according to one aspect of the subject technology.
Figure 5:
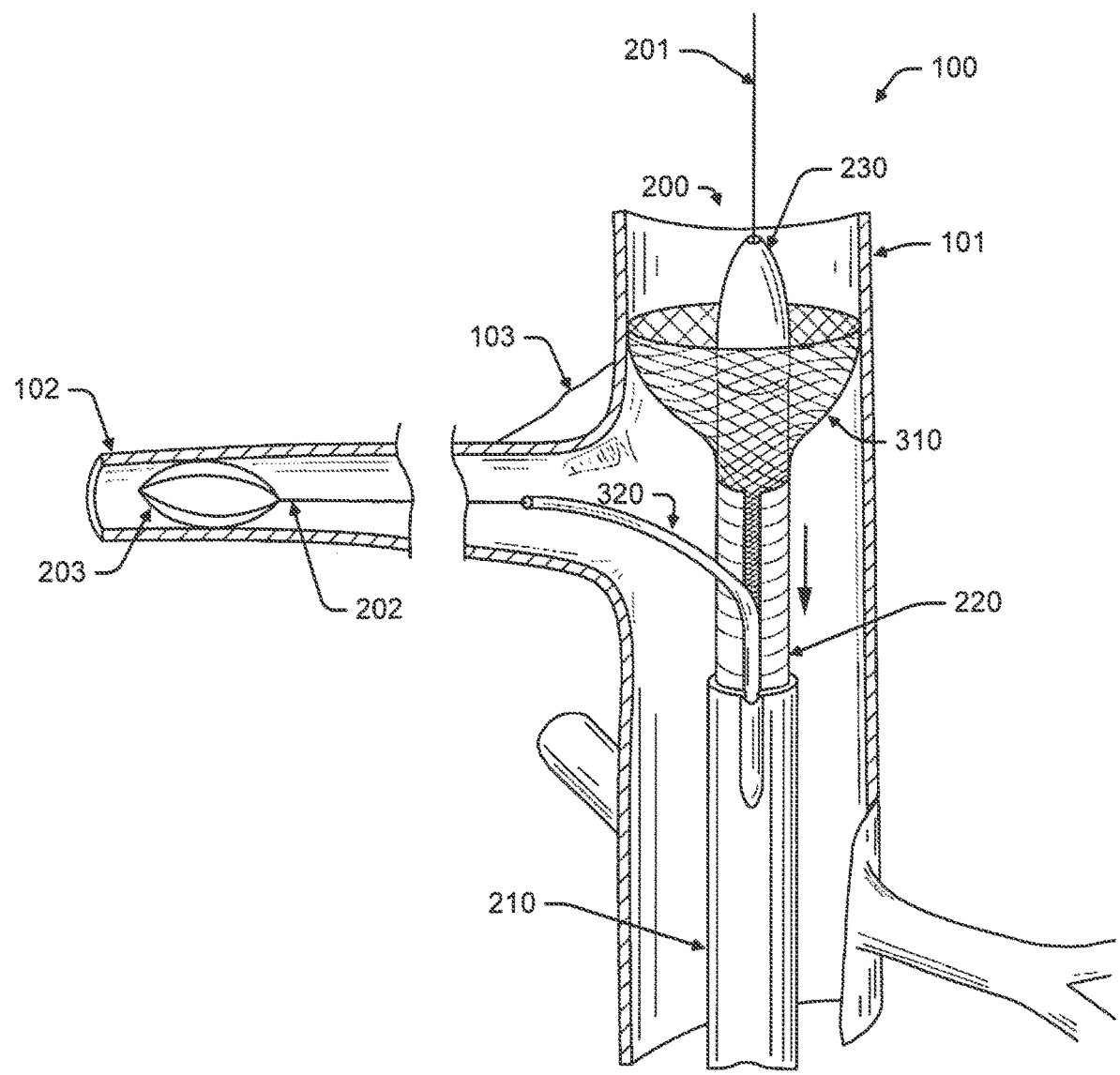
FIG. 5 depicts an endograft delivery system with a delivery catheter withdrawn proximally, according to one aspect of the subject technology.

In one aspect, the main graft assembly 310 and the branch graft assembly 320 may be configured to lie substantially parallel to each other during delivery of the main graft assembly 310 to the main vessel 101. As described further below, upon deployment of the branch graft assembly 320, a proximal portion of the branch graft assembly 320 may remain within and/or in contact with the main graft assembly 310 while a distal portion of the branch graft assembly 320 may move away from the main graft assembly 310, as shown in FIGS. 3-5.

Figure 12:
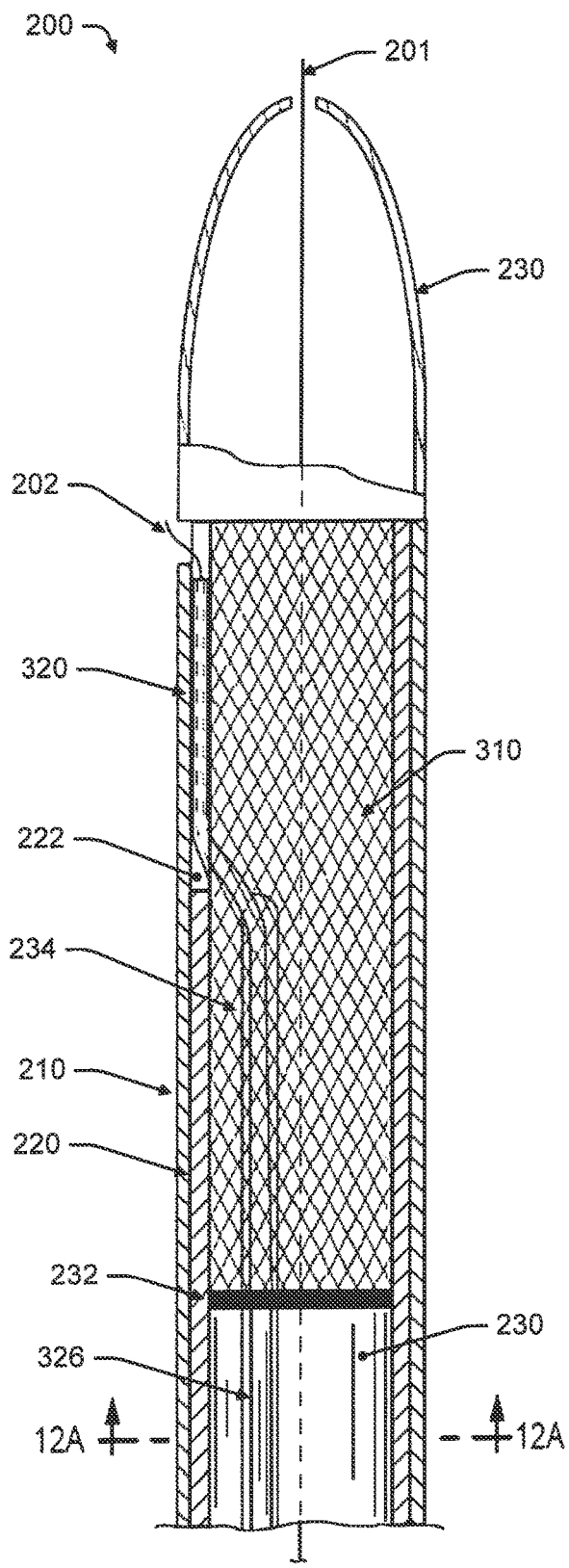
FIG. 12 depicts a partial cross section view of an endograft delivery system, according to one aspect of the subject technology.
Figure 12A:
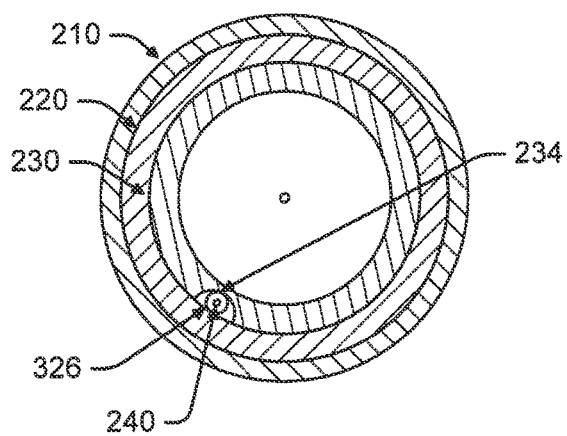
FIG. 12A depicts a cross section side view of an endograft delivery system, according to one aspect of the subject technology.

FIG. 12 is a partial cross-section side view of an endograft delivery system 200, which can be used to deploy the main graft assembly 310 and the branch graft assembly 320 described above. The main graft assembly 310 and the branch graft assembly 320 may be delivered to a treatment site using the delivery system 200, which allows for retrograde deployment of the branched endograft 300 from the femoral artery. Other distal vessels, however, may be utilized for deployment.

The delivery system 200 may comprise an elongate flexible multi-component structure comprising an outer sheath 210, a delivery catheter 220, a pusher 240, a main delivery member 201, a branch delivery member 202, and an anchoring member 203.

Figure 13:
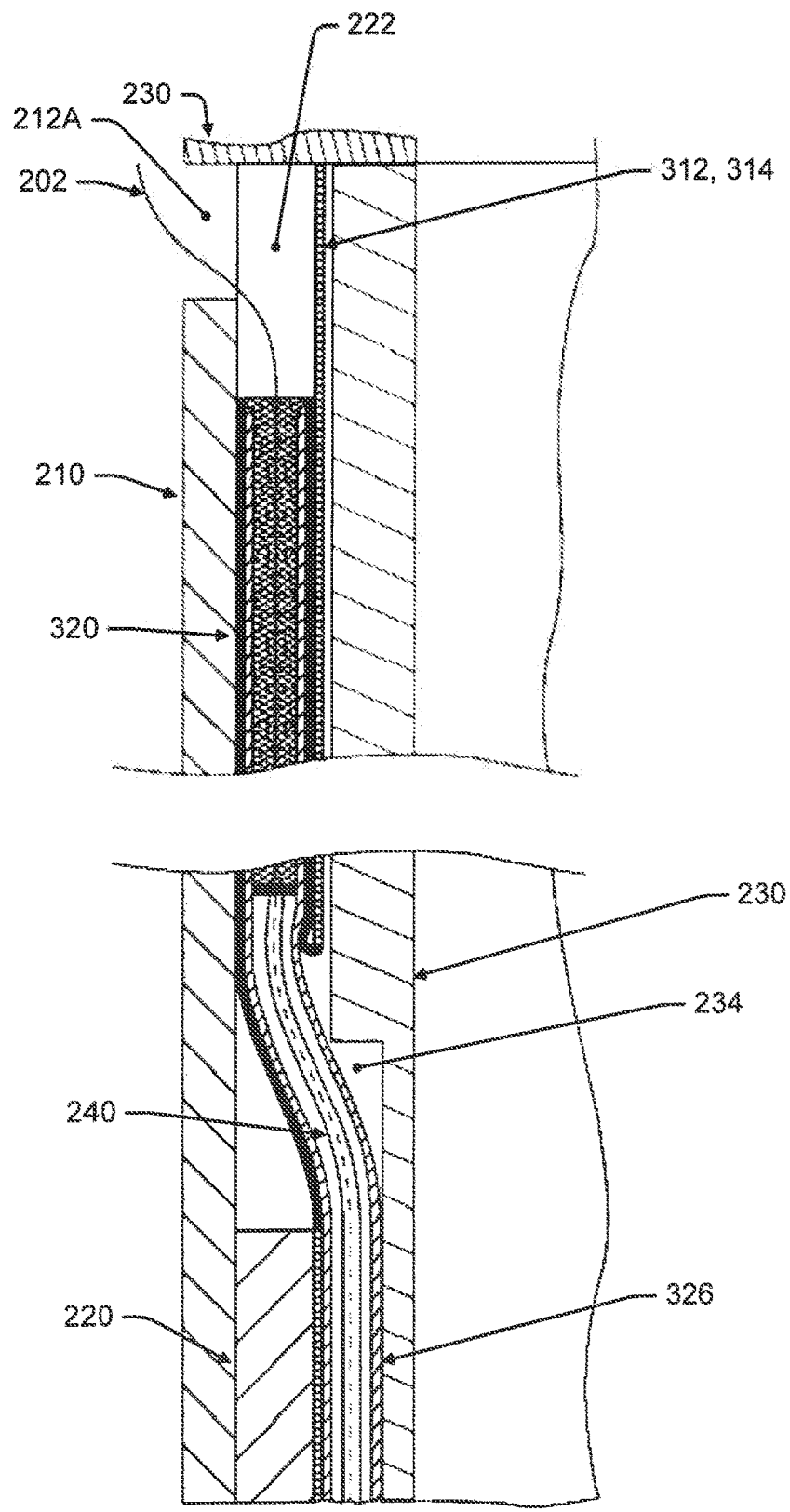
FIG. 13 depicts a detailed cross section of an endograft delivery system, according to one aspect of the subject technology.
Figure 14:
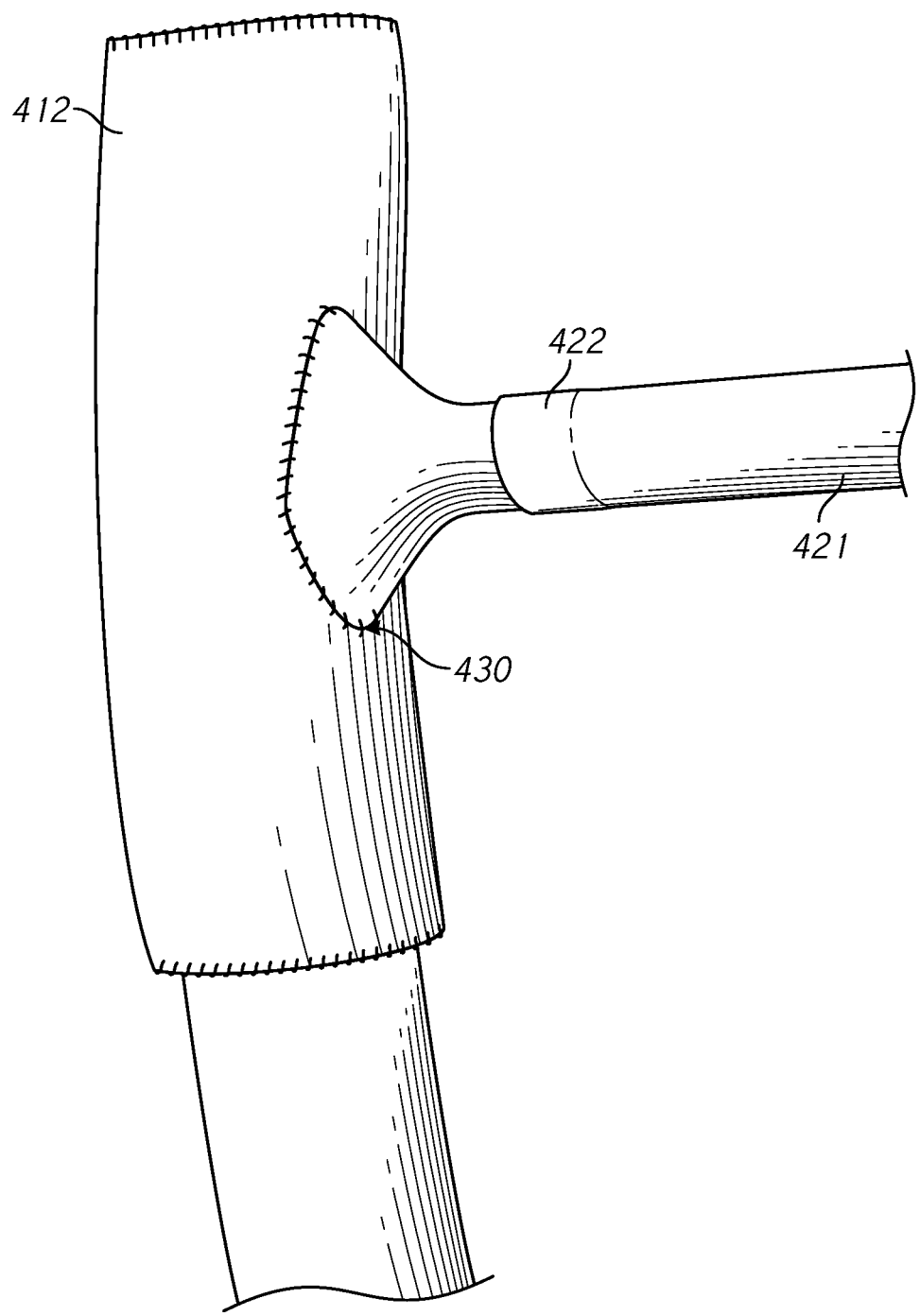
FIGS. 14-18 depict a branch endograft fabric "cover" that branches from a main endograft fabric "cover" and tapers from a relatively wide cross-sectional dimension at the branch ostium to a narrower cross-sectional dimension along more distal portions of the branch endograft's axial length.
Figure 15:
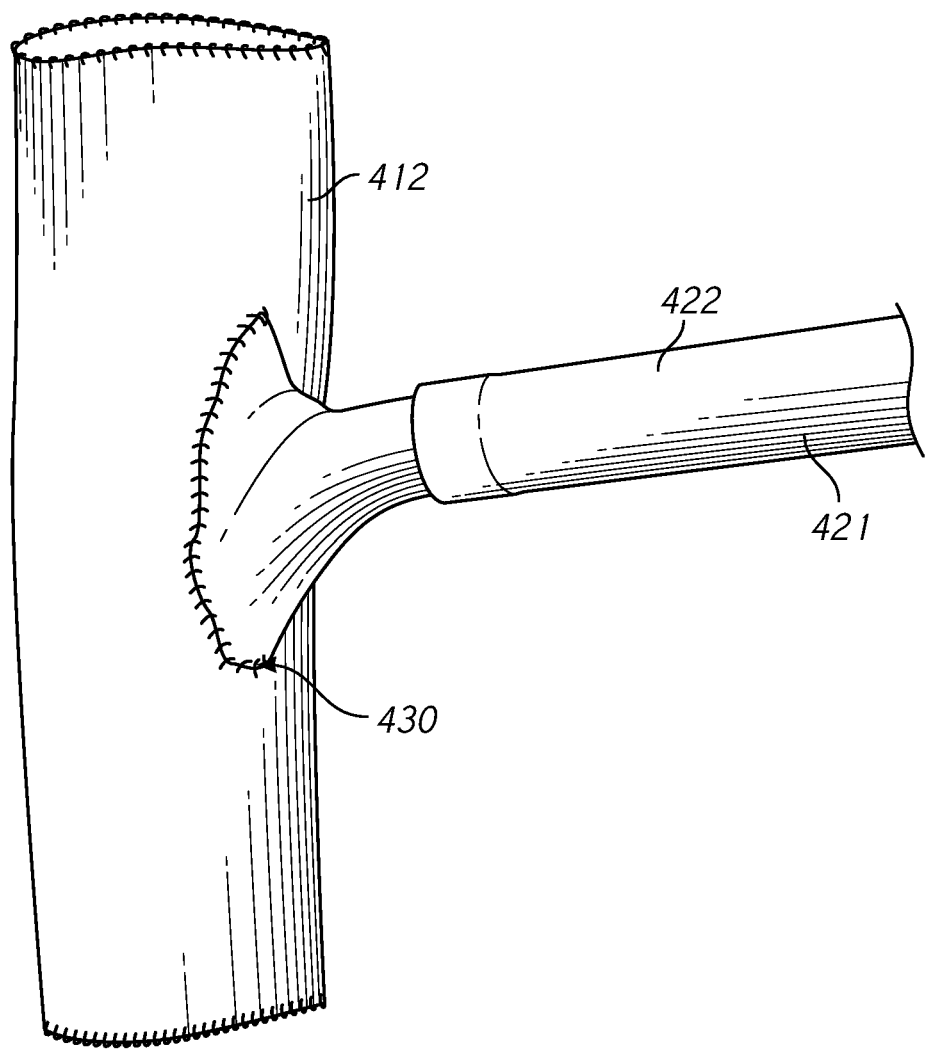
Figure 16:
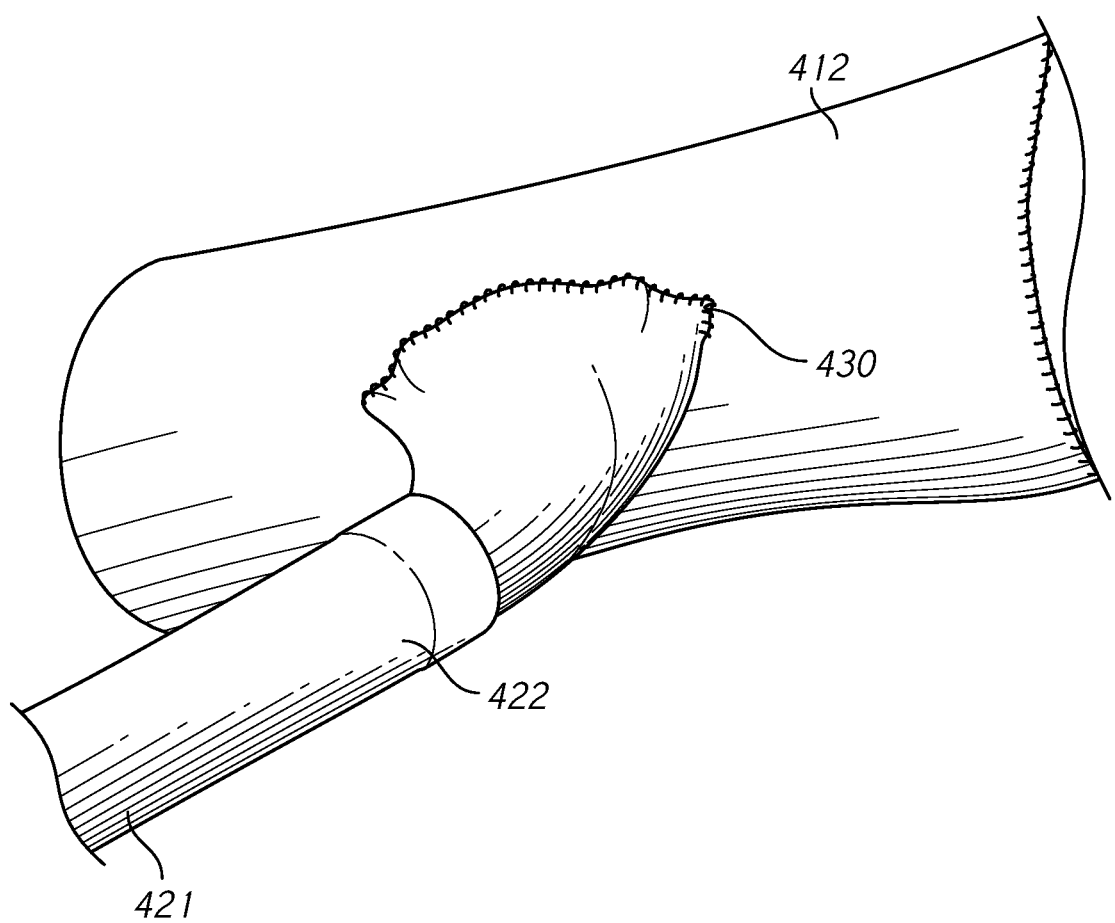
Figure 17:
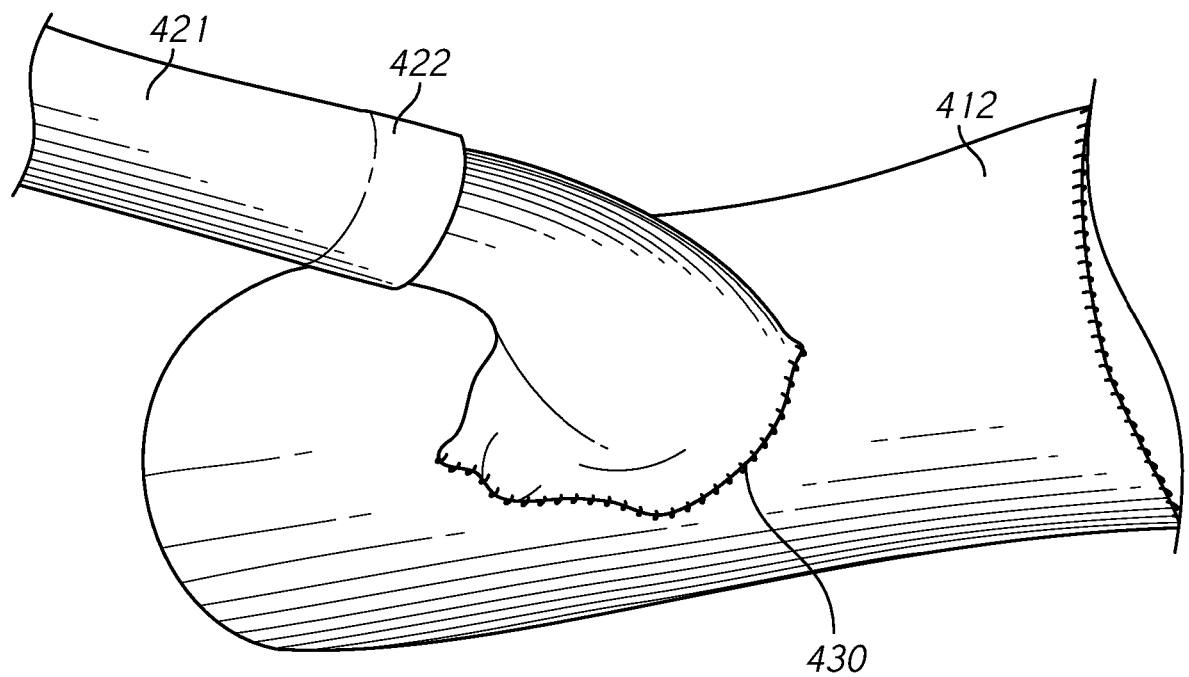
Figure 18:
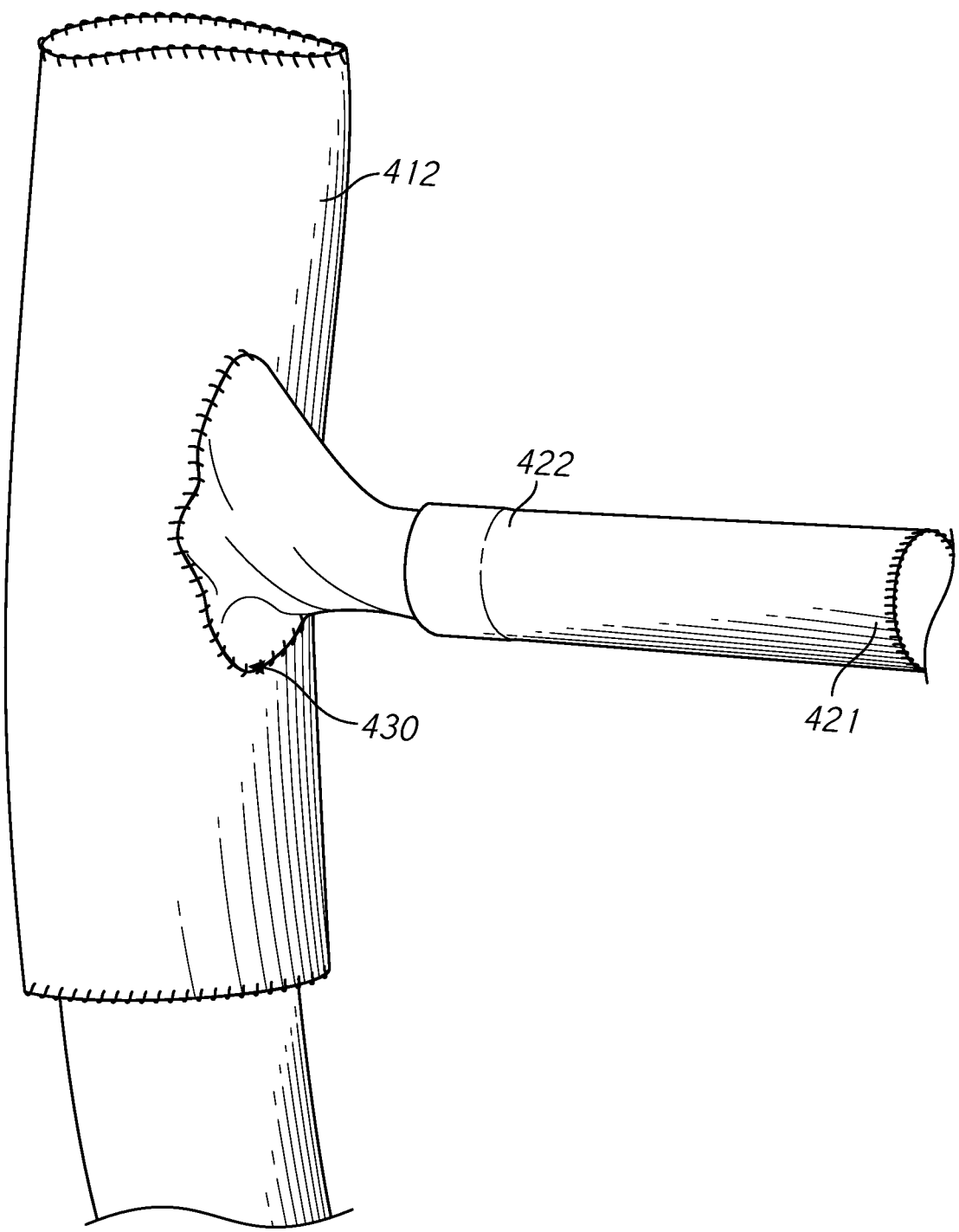

Referring to FIG. 13, the outer sheath 210 may be configured to compress or constrain the expansion of the branch graft assembly 320 by at least partially surrounding the branch graft assembly 320. The outer sheath 210 may also be configured to at least partially surround the delivery catheter 220. The outer sheath 210 may be manufactured from biocompatible materials and may be provided with a proximal hub or valve.

Figure 2:
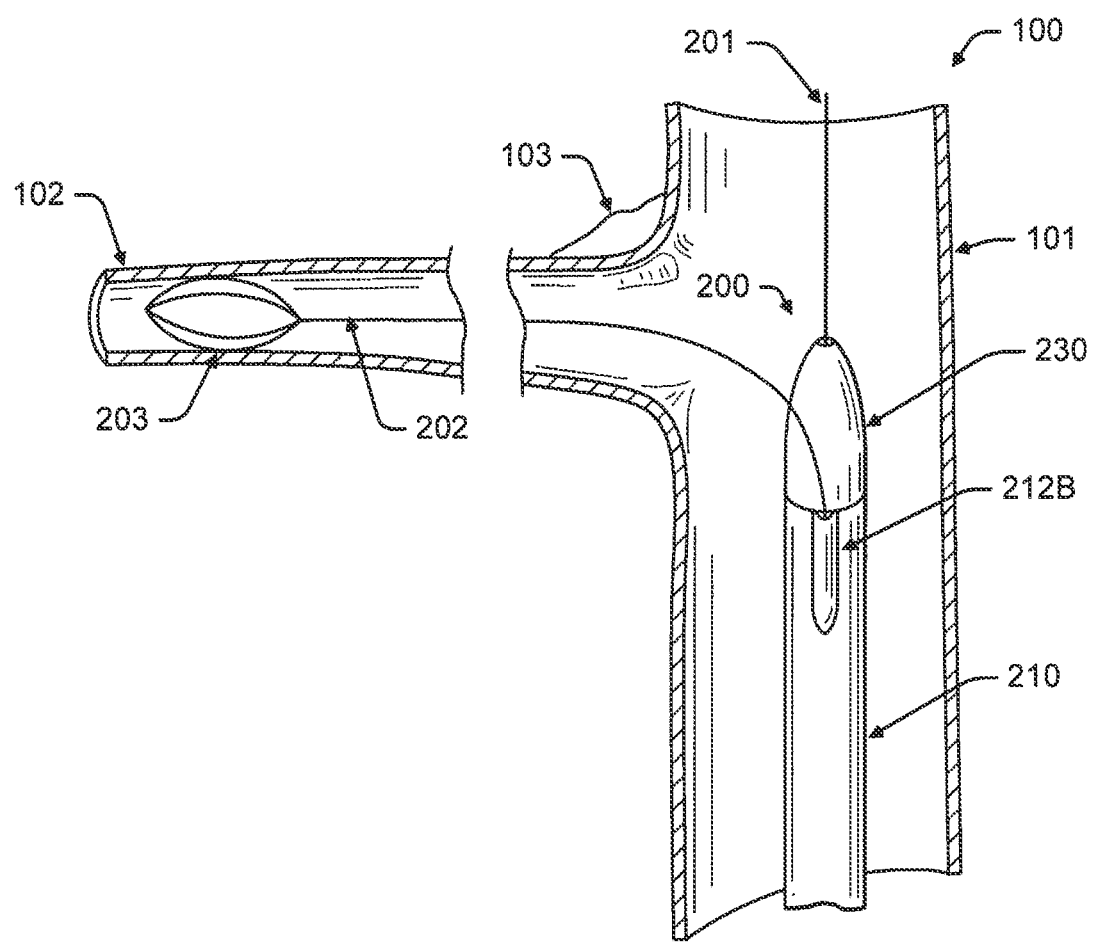
FIG. 2 depicts an endograft delivery system, according to one aspect of the subject technology.

In one aspect, a distal end of the outer sheath 210 may have a cutout 212A, longitudinal protrusion 212B (as shown in FIG. 2), or aperture to provide clearance for the branch delivery member 202 to extend therethrough, as shown in FIG. 13. In another aspect, the outer sheath 210 may include a stop (not shown) configured to limit distal movement of the outer sheath 210 with respect to the delivery catheter 220 such that a gap 212A may be formed between the outer sheath 210 and the delivery catheter 220 to provide sufficient clearance for the branch delivery member 202 to extend therethrough. In one aspect, the protrusion 212B may provide an area for the branch graft assembly 320 to reside within. As will be explained in detail below, proximal retraction of the outer sheath 210 with respect to the delivery catheter 220 will deploy the branch graft assembly 320. Accordingly, the outer sheath 210 may be axially movably positioned with respect to the delivery catheter 220.

The delivery catheter 220 may be configured to extend through the outer sheath 210 and deploy the main graft assembly 310. The delivery catheter may comprise a delivery sheath 220 and an inner elongate member 230. The delivery sheath 220 and the elongate member 230 may be manufactured from biocompatible materials. The main graft assembly 310 may be positioned in a compressed or reduced diameter state within the delivery sheath 220, between the delivery sheath 220 and the elongate member 230. As will be explained in detail below, proximal retraction of the delivery sheath 220 with respect to the elongate member 230 will deploy the main graft assembly 310. Accordingly, the delivery sheath 220 may be axially movably positioned within the outer sheath 210.

The delivery sheath 220 may be configured to at least partially surround the main graft assembly 310 and keep the main graft assembly 310 in a compressed configuration during passage through various vessels to the treatment site 100. The delivery sheath 220 may include a plurality of reinforcing ribs or supports to further aid in maintaining the main graft assembly 310 in the compressed configuration.

A distal end of the delivery sheath 220 may have an aperture, longitudinal slot or groove 222 to accommodate the branch graft assembly 320 in a compressed configuration during passage through various vessels to the treatment site 100. The groove 222 may also assist in minimizing the diameter of the outer sheath 210 by accommodating the branch graft assembly 320 within the groove 222. In one aspect, the branch sheath 326 may extend through the groove 222, as shown in FIG. 13.

The elongate member 230 may have a tapered distal tip to minimize damage to the vessel wall during passage through various vessels to the treatment site. The elongate member 230 may extend within the delivery sheath 220 and may be configured to resist proximal and/or distal movement of the main graft assembly 310 within the delivery sheath 220. For example, the elongate member 230 may have a circumferential rib 232 configured to engage the proximal end 315 of the main graft assembly 310. The elongate member 230 may have a lumen for allowing the main delivery member 201 to extend therethrough. In one aspect, the elongate member 230 may have an indent 234 for accommodating the branch sheath 326, as shown in FIGS. 6-9, 12 and 12A.

The main delivery member 201 may be a guide wire configured to extend through the, outer sheath 210, the delivery catheter 220, and the main graft assembly 310, into the main vessel 101.

The branch delivery member 202 may be a guide wire configured to extend through the outer sheath 210, the delivery catheter 220, the branch cover 322, the branch stent 324, and the branch sheath 326, and the pusher 240, into the branch vessel 102.

Referring to FIGS. 11 and 13, the pusher 240 may extend within the branch sheath 326 and may be configured to resist proximal movement of the branch stent 324 within the branch sheath 326. The pusher 240 may comprise a flexible tubular member having a distal end that is configured to engage a proximal end of the branch stent 324 to thereby prevent the compressed branch stent 324 from moving proximally and aid in deployment of the branch stent 324 as the branch sheath 326 is moved proximally. The pusher 240 may also include a lumen for allowing the branch delivery member 202 to extend therethrough.

Referring to FIG. 1, the anchoring member 203 may be disposed at a distal portion of the branch delivery member 202. The anchoring member 203 is configured to expand in and engage the branch vessel 102 to provide an atraumatic tip and resist axial movement of the anchoring member 203 within the branch vessel 102, thereby enabling the branch delivery member 202 to maintain its position within the branch vessel 102 as the branch cover 322 is maneuvered and deployed in the branch vessel 102, as further described below. The anchoring member 203 is configured to engage the branch vessel 102 by applying gentle outward pressure onto the inner surface of the branch vessel 102.

The anchoring member 203 enables deployment of the branch graft assembly in an end organ vessel, such as the renal, superior or inferior mesenteric, celiac, splenic, or hepatic arteries, or biliary or pancreatic ducts. Serving as an atraumatic tip, the anchoring member 203 helps prevent the branch delivery member 202 from puncturing an end organ perfused by the artery into which the anchoring member 203 is inserted.

The anchoring member 203 may be wholly or partially self expandable, e.g., via application of heat or upon release of the anchoring member 203 from a lumen of a constraining member, such as a sheath (not shown). In the later example, the anchoring member 203 may be released by proximal movement of the constraining member relative to the anchoring member 203. The anchoring member 203 may be constructed of multiple flexible curved wire struts so as to take a oblong form. In an alternative embodiment, the anchoring member 203 be expanded via an internal expanding device (e.g., a balloon).

The outer sheath 210, the delivery catheter 220, and the other components of the delivery system 200 can be manufactured in accordance with any of a variety of techniques well known in the catheter manufacturing field. Extrusion of tubular catheter body parts from material such as Polyethylene, PEBAX, PEEK, nylon and others is well understood. Suitable materials and dimensions can be readily selected taking into account the natural anatomical dimensions of the treatment site, together with the dimensions of the desired implant and percutaneous or other access site.

A technique for deploying the branched endograft 300 using the delivery system 200 for treating disease involving branching blood vessels of a mammal will now be discussed with reference to FIGS. 1-9. The treatment may, for example, comprise treating an aortic aneurysm. As shown in FIG. 1, two guide wires, the main delivery member 201 and the branch delivery member 202 are used for the deployment of the main graft assembly 310 and the branch graft assembly 320. The main delivery member 201 may be used to guide the outer sheath 210, together with the delivery catheter 220 and the branched endograft 300, to the main vessel 101, which may be introduced through an arterial catheter. The branch delivery member 202 may be used for the deployment of the branch cover 322 into the branch vessel 102.

The main delivery member 201 and the branch delivery member 202 may comprise a standard 0.035" diameter guide wire. The main delivery member 201 and the branch delivery member 202 may be introduced, for example, through a percutaneous puncture via a sheath, and advanced superiorly towards the aneurysm 103 and the treatment site 100. In one embodiment, the percutaneous puncture is formed on the femoral artery. The main delivery member 201 is preferably positioned across the aneurysm and into the main vessel 101. The branch delivery member 202 is preferably positioned in the branch vessel 102.

The branch delivery member 202, including the anchoring member 203, may be introduced through a catheter, which constrains or compresses the anchoring member 203 until it is positioned correctly in the branch vessel 102. The catheter or constraining member is then retracted, via proximal movement of the constraining member relative to the anchoring member 203, to allow the anchoring member 203 to gently expand and engage the branch vessel 102.

An advantage of the subject technology is that it permits delivery and subsequent deployment (by unsheathing) of the branch graft assembly 320 and the main graft assembly 310 into blood vessels via a single vascular access puncture. There is no need to use a second vessel puncture to unsheath either graft assembly.

Referring to FIG. 2, after the main delivery member 201 and the branch delivery member 202 are in position, the main delivery member 201 and the branch delivery member 202 are threaded through the appropriate lumens in the delivery system 200. For example, as described above, the main delivery member 201 extends through at least the lumen of the elongate member 230 and the branch delivery member 203 extends at least through the cutout 212A (as shown in FIG. 13) or longitudinal protrusion 212B of the outer sheath 210 and the lumen of the pusher 240 (as shown in FIG. 11).

The outer sheath 210, together with the delivery catheter 220 and the branched endograft 300, may then be advanced over the main delivery member 201 until the distal end of the delivery catheter 220 is positioned at or near the treatment site 100. During this step, the outer sheath 210 surrounds the delivery catheter 220 and houses the main graft assembly 310 and the branch graft assembly 320.

As shown in FIG. 3, once the distal end of the delivery catheter 220 is in the vicinity of the branch vessel 102, the branch graft assembly 320 may be deployed. The branch graft assembly 320 may be deployed by proximally withdrawing the outer sheath 210, thereby exposing the delivery catheter 220 and unconstraining the distal portion of the branch graft assembly 320 to allow the branch graft assembly 320 to articulate. In one aspect, the groove 222 provides the branch graft assembly 320 with sufficient clearance as to enable the distal portion of the branch graft assembly to be movable within the groove 222.

The coupling region 330 allows the branch graft assembly 320 to articulate and permits sufficient flexibility between the main graft assembly 310 and the branch graft assembly 320 such that the branch graft assembly 320 may be positioned within the branch vessel 102 while the main graft assembly 310 is positioned within the main vessel 101.

Referring to FIG. 4, as the delivery system 200 is advanced using the main delivery member 101, the branch graft assembly 320 is guided by the branch delivery member 202 into the branch vessel 102.

Figure 6:
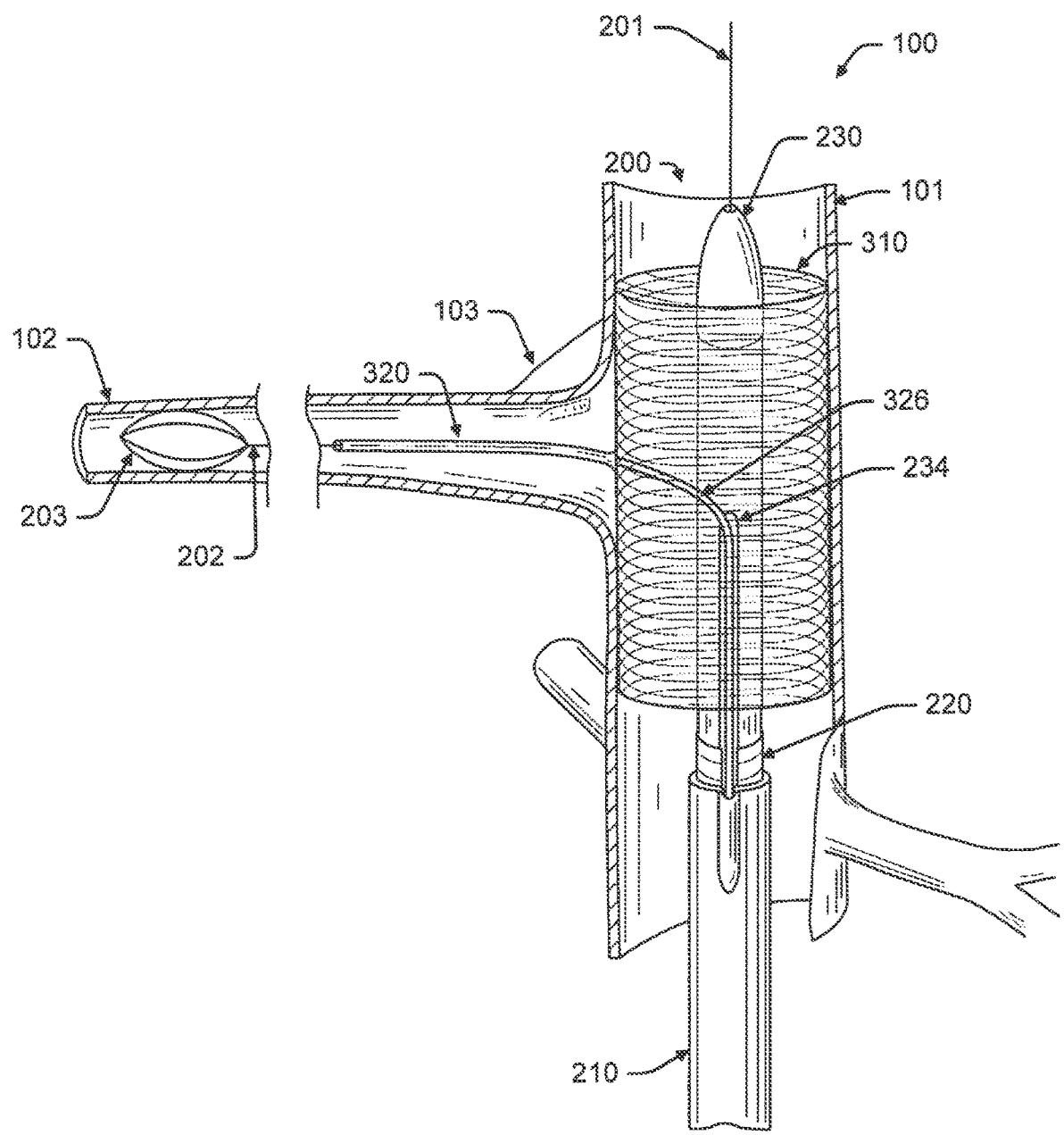
FIG. 6 depicts a deployed main graft assembly, accordingly to one aspect of the subject technology.

Referring to FIG. 5, once the delivery catheter 220 is in the deployment location, the delivery sheath 220 may be proximally withdrawn thereby allowing the main graft assembly 310 to expand within the main vessel 101. Further proximal retraction of the delivery sheath 220 exposes the main graft assembly 310 allowing it to expand, spanning at least a portion of the aneurysm 103. Referring to FIG. 6, in one aspect, expansion of the main graft assembly 310 may further push the branch graft assembly 320 into the branch vessel 102.

Figure 7:
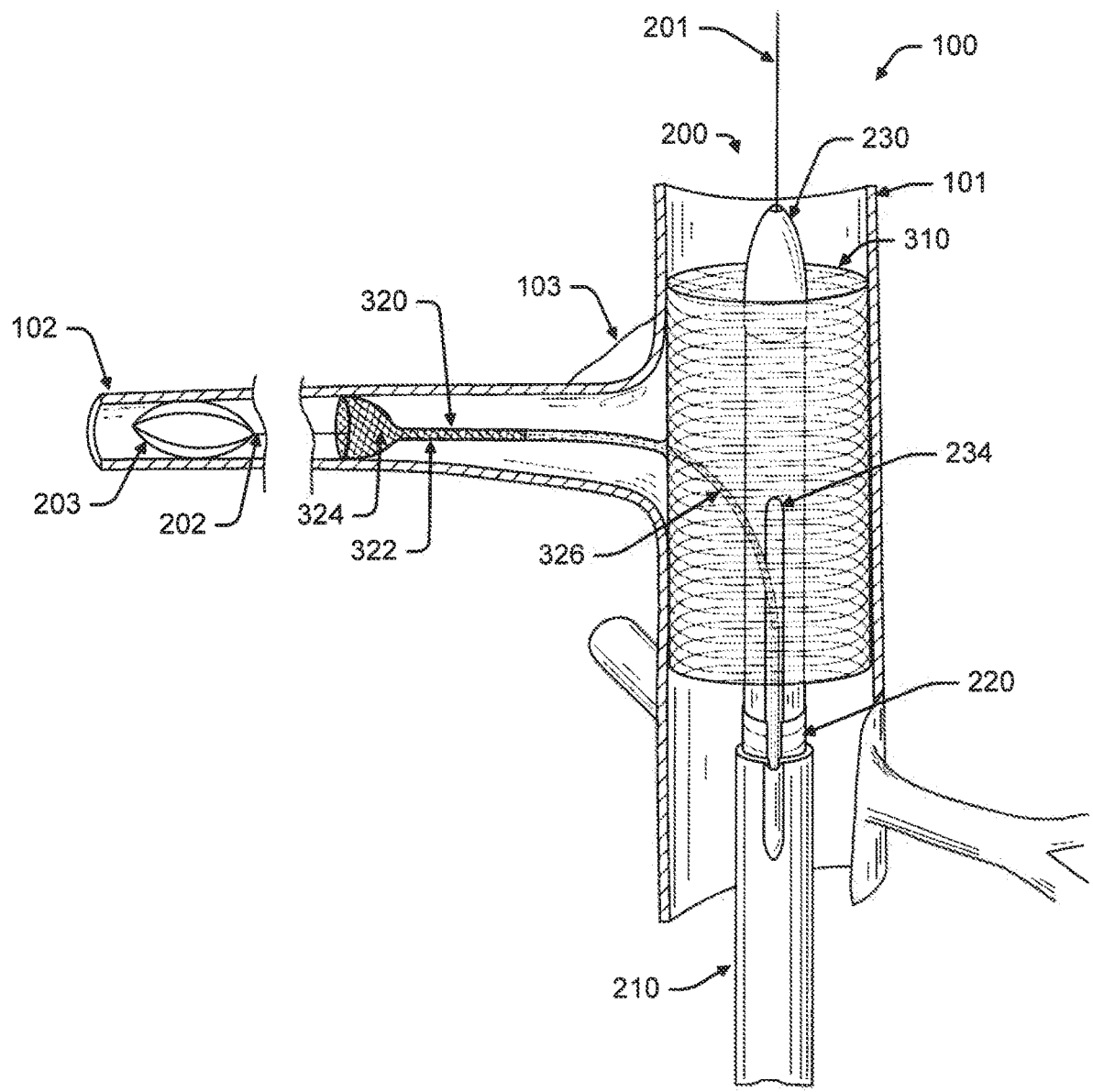
FIG. 7 depicts a branch graft assembly being deployed by an endograft delivery system, according to one aspect of the subject technology.
Figure 8:
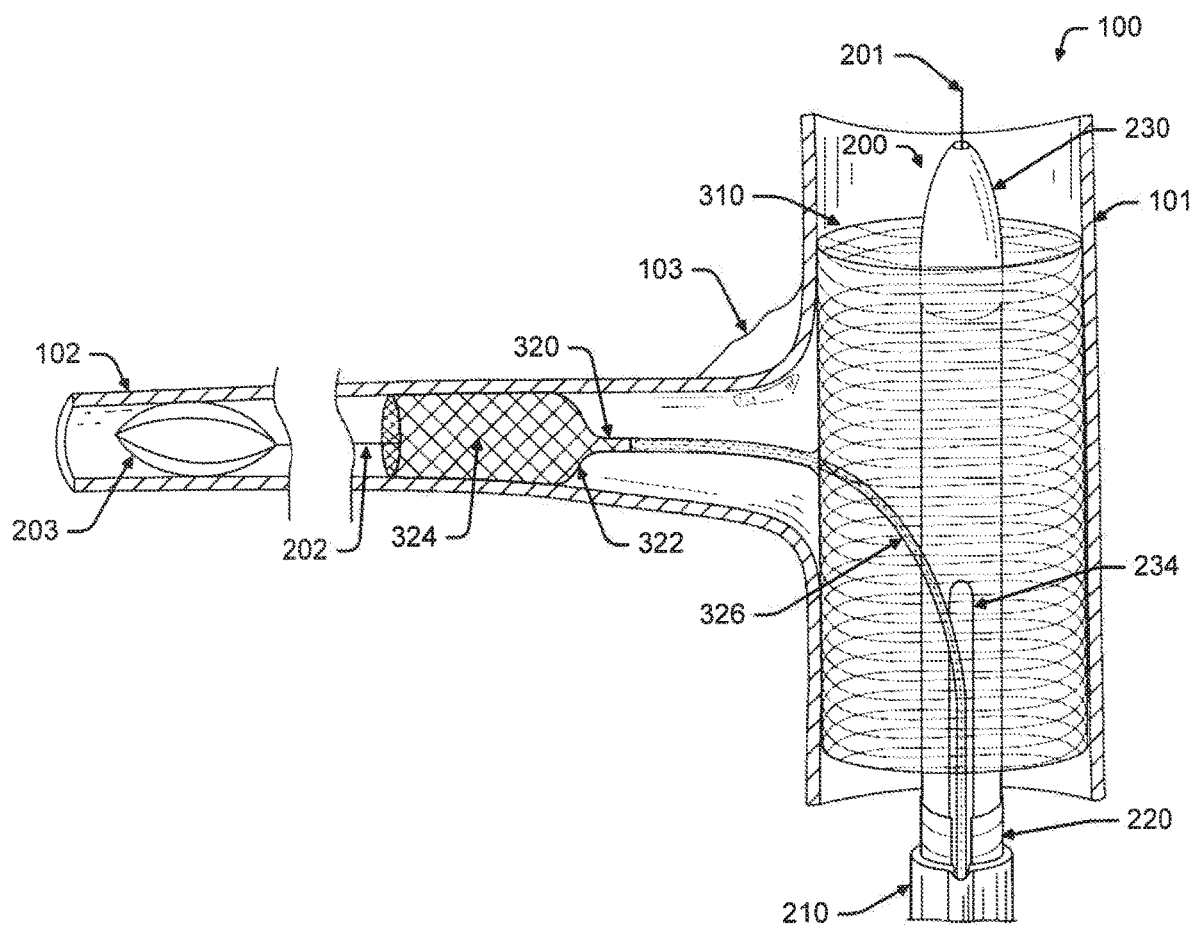
FIG. 8 depicts a branch graft assembly being deployed by an endograft delivery system, according to one aspect of the subject technology.

Referring to FIG. 7, after deployment of the main graft assembly 310, the branch sheath 326, which extends outside of the main graft assembly 310 and within the branch graft assembly 320, may be proximally withdrawn to thereby allow the branch stent 324 to expand radially within and against the branch cover 322. Expansion of the branch stent 324 causes the branch cover 322 to also expand within the branch vessel 102. Referring to FIG. 8, further proximal retraction of the branch sheath 326 exposes the branch stent 324 allowing both the branch cover 322 and the branch stent 324 to expand in the branch vessel 102. The pusher 240 resists proximal movement of the branch stent 324 during retraction of the branch sheath 326. In addition, because the branch stent 324 is coupled 323 to distal end 321 of the branch cover 322, as shown in FIG. 11, the branch stent 324 is maintained in position. Further, distal movement of the branch sheath 326 within the branch cover 322 is inhibited by the coupling 323 of the branch stent 324 to the branch cover 322, as described above.

Figure 9:
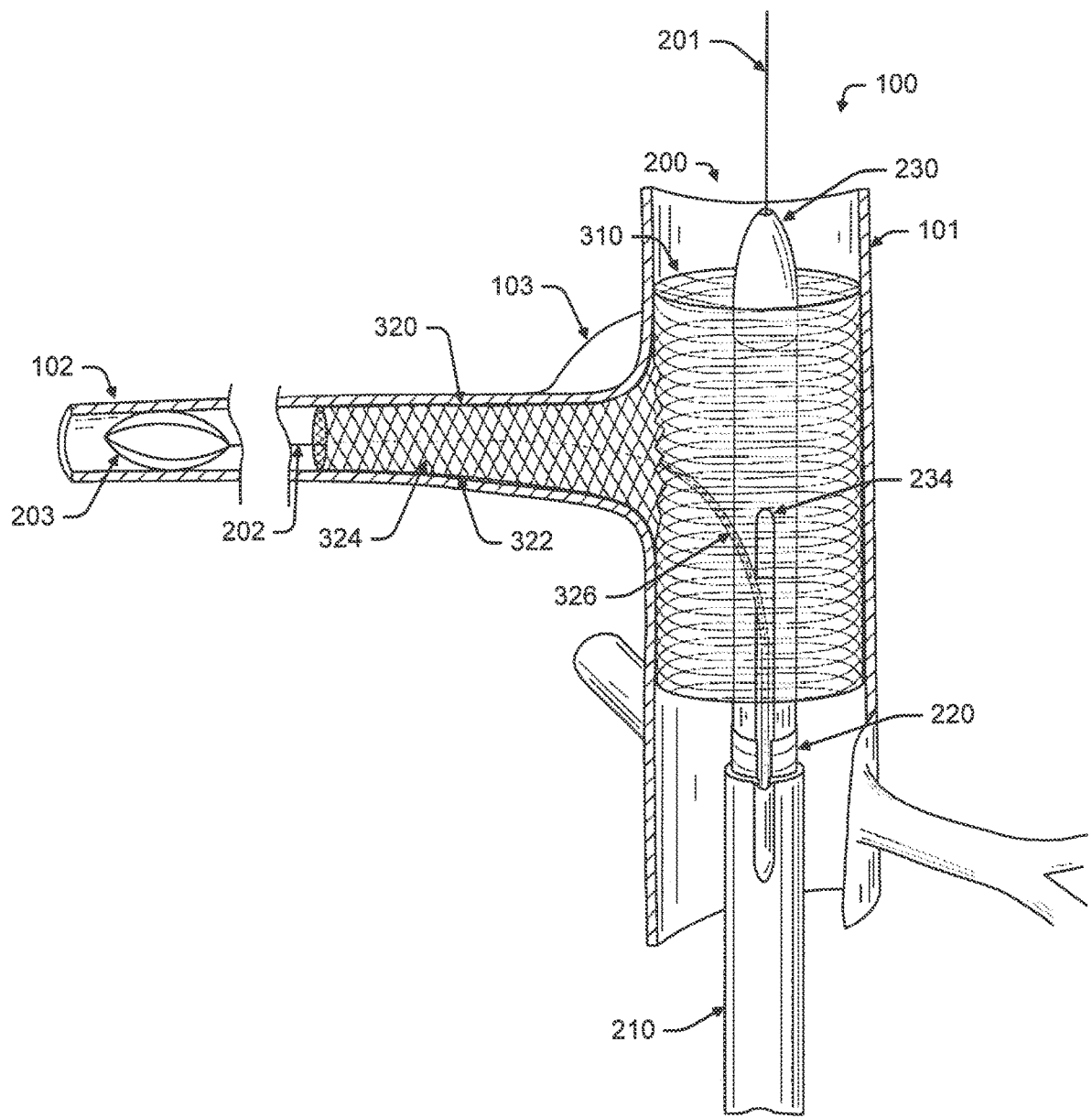
FIG. 9 depicts a deployed branch graft assembly, according to one aspect of the subject technology.

Referring to FIG. 9, after the branch cover 322 is deployed and supported by the branch stent 324, the branch sheath 326, delivery sheath 220, and/or the elongate member 230 may be retracted into the outer sheath 210 for removal. With the main graft assembly 310 deployed, the delivery sheath 220 and/or the elongate member 230 may be proximally withdrawn through the deployed main graft assembly 310. The delivery system 200 may thereafter be proximally withdrawn from the patient by way of the percutaneous access site.

The delivery system 200 and/or the branched endograft 300 may include one or more radio opaque markers such that delivery system 200 and/or the branched endograft 300 may be properly orientated with respect to the anatomy. Any of a variety of techniques may be used to provide radio opaque markers, such as, for example, providing the components of the delivery system 200 and/or the branched endograft 300 with bands or staples made of radio opaque material or dispersing radio opaque material into the material that forms the components of the apparatus.

Although the branched endograft 300 and delivery system 200 have been discussed in the context of treating an aortic aneurysm that has compromised one or more visceral branches of the thoracic or abdominal aorta, the branched endograft and delivery system may be used in any anatomic region. For example, the branched endograft 300 and delivery system 200 may be used to treat not only vascular disease, but disease of other branching vessels of the body, such as bile ducts. End organ branch arteries may also be treated, such as the renal, superior mesenteric, celiac, splenic, or hepatic arteries.

FIGS. 14-18 depict a branch endograft fabric "cover" 422 that branches from a main endograft fabric "cover" 412 and tapers from a relatively wide cross-sectional dimension at the branch ostium 430 to a narrower cross-sectional dimension along more distal portions 421 of the branch endograft's axial length. Due to fabric laxity in this illustrated case, the branch cover 422 can move relatively freely axially, radially, and rotationally along its long axis to accommodate placement in a branch artery (e.g, a renal artery) whose ostium at a main vessel (e.g., the aorta) is axially and/or radially misaligned with the branch graft cover's ostium 430.

Figure 19:
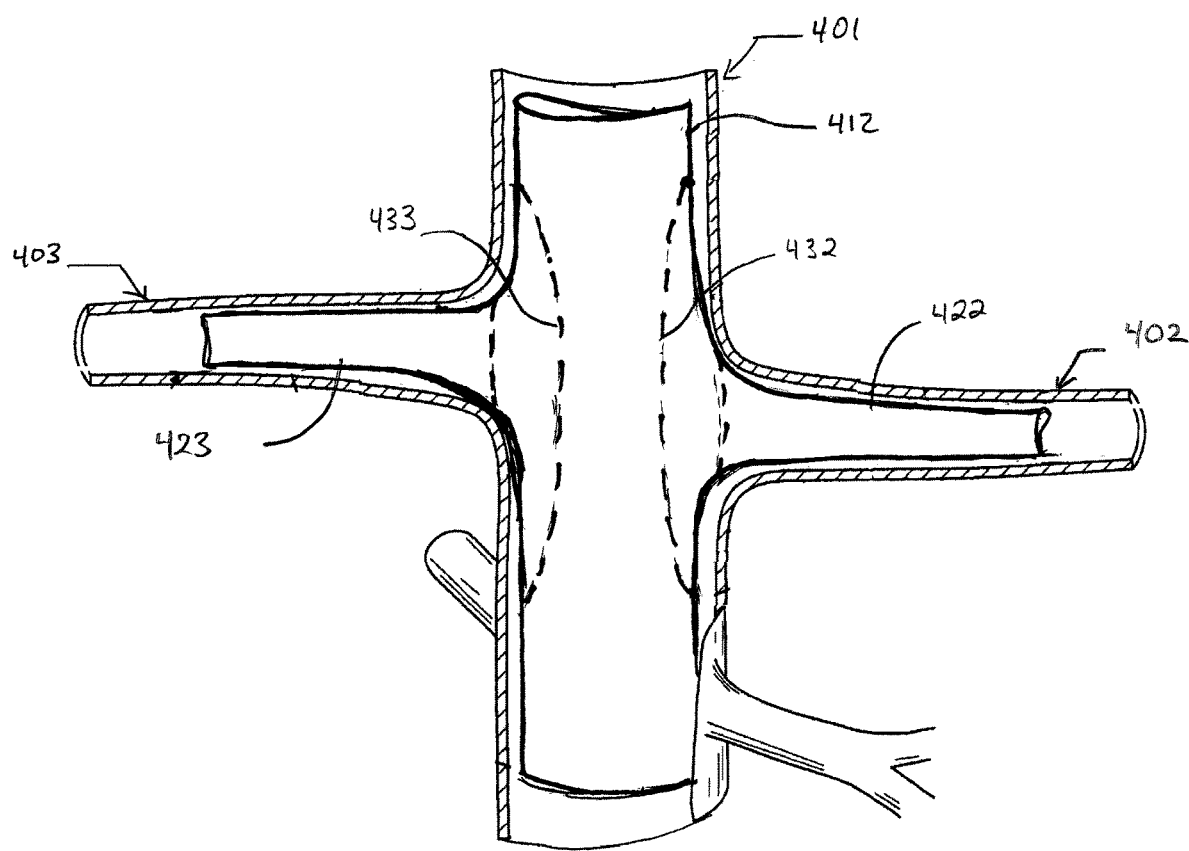
FIG. 19 depicts a branch endograft assembly according to the subject technology, with the main cover placed in the aorta, and two branch covers cover placed in bilateral renal arteries having axially asymmetric ostia.

FIG. 19 depicts a branch endograft assembly according to the subject technology, with the main cover (illustrated as a fabric) 412 placed in the aorta 401, and two branch covers cover 422 and 423 (illustrated as a fabric continuous with the main cover) placed in bilateral renal arteries (e.g., left renal artery 402 and right renal artery 403) having symmetric take-offs or ostia 432 and 433 (i.e., symmetric take-off points, or regions, relative to an axial length and/or radial orientation of the aorta). Having fabric of sufficient (redundant) length and flexibility, the left branch 422 cover is shown as axially shifted somewhat to permit blood to flow into the left renal artery 402, which has a more superiorly oriented ostium (or take-off) than that of the right renal artery 403.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There can be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A method for placing an endograft assembly in an aorta having branching vessels, said method comprising:
    providing an endograft including a main cover, a first branch cover, and a second branch cover;
    implanting the endograft in the aorta between opposed branching vessels or covering adjacent branching vessels, wherein the first branch cover and the second branch cover move relatively freely axially, radially, and rotationally relative to a long axis of the main cover to accommodate different positions of the branching vessels.

2. A method as in claim 1, wherein the main cover expands in the aorta to contact a wall of the aorta.

3. A method as in claim 2, wherein the main cover further expands to contact a wall of the at least one of the first and second branching vessels.

4. A method as in claim 3, wherein the main cover further expands to contact the walls of both branching vessels.

5. A method as in claim 1, wherein each branch cover is tapered from a wide cross-section at its base where connected to the main cover to a narrower cross-section along more distal portions thereof.

6. A method as in claim 1, wherein each branch cover is integrally formed with the main cover.

7. A method as in claim 1, wherein each branch cover and the main cover comprise a fabric.

8. A method as in claim 1, further comprising expanding a main stent within a lumen of the main cover and a branch stent within a lumen of each branch cover.

9. A method as in claim 1, wherein the first and second branching vessels are renal arteries having asymmetric ostia.

10. A method as in claim 9, wherein the main cover is first expanded in the aorta, the first branch cover is aligned with and expanded in a first renal artery, and the second branch cover moves axially, radially and/or rotational to align with the second renal artery before expansion.

11. A method as in claim 1, wherein the first and second branching vessels are aortic arch vessels having axially adjacent ostia.

* * * * *